(12) United States Patent
Hecht et al.

(10) Patent No.: US 8,091,432 B2
(45) Date of Patent: Jan. 10, 2012

(54) MONITORING SYSTEM FOR CONCRETE PILINGS AND METHOD OF INSTALLATION

(75) Inventors: Kurt Hecht, Buckingham, PA (US); Richard Hecht, Tewksbury, MA (US)

(73) Assignee: Smart Structures, Inc., Gainesville, FL (US)

( * ) Notice: Subject to any disclaimer, the term of this patent is extended or adjusted under 35 U.S.C. 154(b) by 33 days.

(21) Appl. No.: 12/637,863

(22) Filed: Dec. 15, 2009

(65) Prior Publication Data

US 2010/0092247 A1 Apr. 15, 2010

Related U.S. Application Data

(62) Division of application No. 11/188,492, filed on Jul. 25, 2005, now Pat. No. 7,637,166.

(60) Provisional application No. 60/685,807, filed on May 31, 2005, provisional application No. 60/642,585, filed on Jan. 10, 2005, provisional application No. 60/590,955, filed on Jul. 23, 2004.

(51) Int. Cl.
*G01N 3/00* (2006.01)
(52) U.S. Cl. .......................................................... 73/803
(58) Field of Classification Search ..................... 73/803
See application file for complete search history.

(56) References Cited

U.S. PATENT DOCUMENTS

| | | | |
|---|---|---|---|
| 3,571,835 A * | 3/1971 | Buechler ........................ 14/77.1 |
| 4,052,884 A | 10/1977 | Milberger et al. | |
| 4,171,563 A | 10/1979 | Withoos | |
| 4,365,306 A * | 12/1982 | House et al. ................... 702/176 |
| 4,586,366 A * | 5/1986 | Milberger ...................... 73/11.03 |
| 4,943,930 A * | 7/1990 | Radjy ............................. 702/33 |
| 5,099,696 A * | 3/1992 | Yabuuchi ........................ 73/784 |
| 5,172,587 A * | 12/1992 | Long ................................. 73/84 |
| 5,581,013 A | 12/1996 | Frederick | |
| 5,625,993 A * | 5/1997 | Kelly .............................. 52/704 |
| 5,978,749 A | 11/1999 | Likins et al. | |
| 6,127,937 A | 10/2000 | Carlini, Jr. | |
| 6,301,551 B1 | 10/2001 | Piscalko et al. | |
| 6,311,567 B1 * | 11/2001 | England ........................... 73/806 |
| 6,533,502 B2 | 3/2003 | McVay et al. | |
| 6,772,091 B1 | 8/2004 | Robers | |
| 6,796,187 B2 | 9/2004 | Srinivasan et al. | |
| 7,156,188 B2 * | 1/2007 | Bermingham et al. ............ 173/2 |
| 7,180,404 B2 | 2/2007 | Kunerth et al. | |
| 7,353,714 B2 * | 4/2008 | England et al. .................. 73/784 |

FOREIGN PATENT DOCUMENTS

JP 7263949 10/1995

* cited by examiner

*Primary Examiner* — Lisa Caputo
*Assistant Examiner* — Octavia Davis
(74) *Attorney, Agent, or Firm* — Volpe and Koenig, P.C.

(57) ABSTRACT

A system for tracking and monitoring data related to the manufacture, installation and/or life cycle of concrete structures, such as pilings, as well as related system components and methods for tracking, storing and accessing such data is provided. The system utilizes one or more embeddable antenna assemblies as well as sensor packages that are installed in the concrete structure form before casting. The antenna(s) provide wireless communication of the data from the structure. On board memory is also provided to store structure related data with the structure. A system for tracking a pile during driving is also provided.

19 Claims, 23 Drawing Sheets

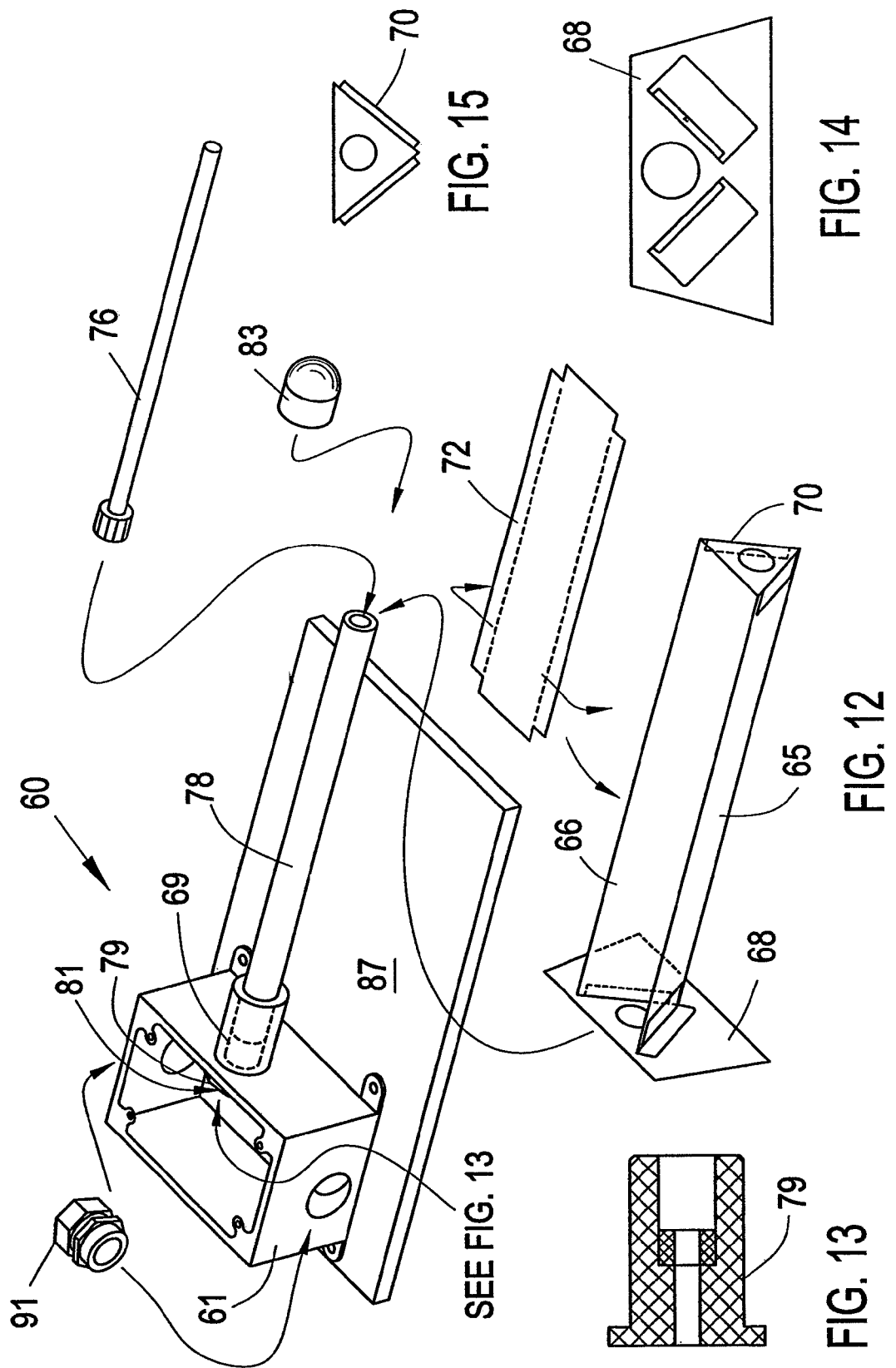

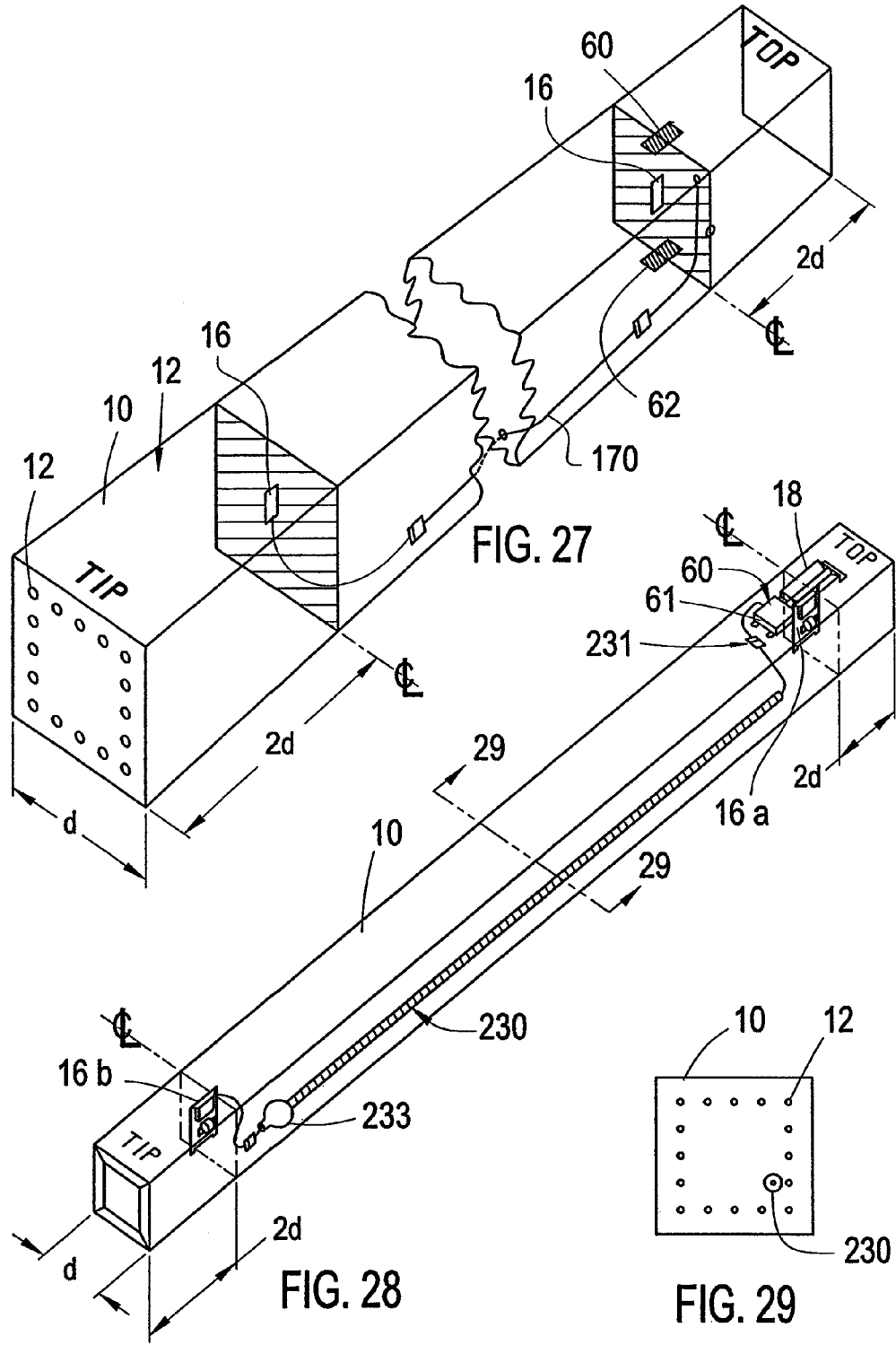

MONITORING SYSTEM FOR CONCRETE PILINGS AND METHOD OF INSTALLATION

CROSS-REFERENCE TO RELATED APPLICATIONS

This application is a divisional of U.S. Ser. No. 11/188,492, filed Jul. 25, 2005 which claims the benefit of U.S. provisional patent 60/685,807, filed May 31, 2005; U.S. provisional patent 60/642,585, filed Jan. 10, 2005; and U.S. provisional patent 60/590,955, filed Jul. 23, 2004, all of which are incorporated herein by reference as if fully set forth.

BACKGROUND

The invention relates to a monitoring system for long term monitoring of concrete pilings and structures, as well as a means of installing and connecting such systems to pilings and structures that have gauges and sensors pre-cast therein.

There is currently no efficient way to communicate information from a concrete structure such as a pile or span, in order to determine conditions related to or generated by installation of such structures. Currently, with concrete structures, such as pilings, that are to be monitored, only approximately one in ten are actually monitored for load bearing and other stress/strain related data due to the significant effort required to manually attach strain gauge/accelerometer monitoring devices to monitor the forces and velocities in the pile during installation. As pilings are generally positioned using choker cables that wrap around the structure that are then lifted by a crane, it is not possible to have anything located on the outside of the piling due to the high risk of it being damaged or cut off by the choker cable during positioning. Currently, after the piling is positioned for driving, the required gauges and sensors are manually attached by climbing to the desired position and attaching them to the standing pile. This is labor intensive, time consuming, costly, and also imposes a safety risk to the installer. As such, only limited monitoring is generally undertaken, resulting in higher design safety factors being required for the structure. A means of performing wireless monitoring at the time of driving would have significant value in reducing the cost and time associated with the testing process, thereby enabling more testing. But there are numerous technical obstacles in doing so, including the wireless transmission of sensor data from the pile.

A basic problem with placing an RF antenna up against, or embedded in concrete is that its performance will be greatly degraded due to the concrete's large dielectric component that varies with the age of the concrete. This presents a very difficult, challenging application environment. With air having a dielectric constant of 1.0, and water 80, concrete varies anywhere from 20 (fresh) to 6 (fully cured after a couple of months depending on water content). The concrete structures in this application are being used about 28 days after cast or sooner, and subsequently were found to have a dielectric constant of about 9.0.

The relatively high dielectric of the concrete placed in close proximity to the RF antenna causes most of the energy emitted from the (now detuned) antenna to be pulled from the antenna and into the concrete. Whatever remaining RF energy coupled to free-air is severely attenuated with distorted and/or erratic patterns, as typical antenna designs are modeled to operate in a free-air environment.

Additionally, after a structural element, such as a pile, is set, no further data is gathered for analysis which could be used for monitoring the long term stability and structural soundness of the structural element in view of cyclic loading and exposure to harsh environments that could cause the structural element to degrade over time, resulting in structural failure.

It would be desirable to provide a more efficient and cost effective method and system for monitoring such concrete structures through the entire useful life of the structure. More preferably, it would be desirable to provide a system that can be easily installed during the casting and manufacturing process which allows monitoring to be done in such a cost effective manner so that all of the concrete structures in a given application, and in particular pilings for buildings, bridges and roadbeds, can be monitored in order to allow for more efficient designs to be utilized without compromising the safety or reliability of the overall structure. Additionally, it would be desirable to provide a system for life-cycle monitoring of such concrete structures, including all concrete structural elements regardless of whether, such as in the case of a piling, the top is cut off after installation. It would also be desirable to provide a means of monitoring embedded gauges regardless of the final state of the structure.

SUMMARY

The invention provides a system for tracking and monitoring data related to the manufacture, installation and/or life cycle of concrete structures, such as pilings, as well as related system components and methods for tracking, storing and accessing such data.

In one aspect of the invention, a permanent, embedded antenna with a reflector is provided that does not protrude from the surface of the structure during fabrication and transport. The antenna is inserted flush to a sidewall of the concrete structure, and extends only to a limited extent into the structure from the outside surface, so that structural integrity is not compromised. Additionally, the antenna is spaced away from the internal steel skeleton of the structure to prevent moisture ingress and the associated structural integrity loss.

The antenna mounting/design must withstand a repetitive, high-shock application environment, characterized by a high number of hammer blows with g-forces of up to about +/−1000 g's. For example, as seen during driving of reinforced concrete pilings.

Additionally, the antenna is subject to an outdoor operating environment including exposure to moisture, and does not hold or retain moisture, as this would impair or disable antenna performance.

The antenna of the invention is permanently embedded in the structure, and subsequently disposable and of low cost.

According to another aspect of the invention, an antenna arrangement is provided that is embedded below the surface of the concrete structure during fabrication. The antenna arrangement includes an actuator that moves the antenna from a first, stowed position, to a second, extended position in which it protrudes from the surface of the concrete surface. The actuator can be manual or can be triggered by a certain load or an oriented shock wave transmitted through the concrete structure, such as the first blow(s) of a pile driving hammer, or through a control command or other electrical signal.

The present invention also provides an economical and fast method of installing sensors and gauges in an easy and repeatable manner in a piling form prior to casting using a U-bar suspension assembly. The U-bar suspension assembly provides for vertical placement of the sensor/gauge package reducing the possibility of damage to the sensor/electronics during casting, and preferably automatically centers the sensor/gauge package in the piling form prior to casting, ensuring the accuracy of the sensor reading.

The invention also provides history tracking and recording memory to allow tracking of piling information throughout installation of the piling, which can also be used to provide active feedback to workers during installation.

The present invention also provides a method of life-cycle monitoring for pilings in addition to other concrete structural elements. The method includes inserting one or more sensor/gauge packages between strands in a piling form to position sensors in a piling core area. These can be, for example, strain gauges, accelerometers, core pressure, temperature and/or moisture sensors and the like. The piling is then cast, encapsulating the sensors. Preferably, a radio/antenna assembly is positioned in the form and pre-cast into the piling as well, with at least the antenna being exposed on a side of the piling near the top. The piling is driven at the construction site, and data is obtained in real time from the sensor/gauge package(s) during driving. This data is transmitted to a control/monitoring system to allow for real time review and analysis of the drive data. After driving, the piling is retrofitted with a networked monitoring node that is connected/interfaced to the existing sensor/gauge package(s). Unique addressing information of a given piling is retained, preferably by logically linking a sensor package address ID. These nodes (and potentially nodes from other sensors in the complete structure) are then connected/networked to an external gateway to allow for life cycle monitoring of some or all of the complete structure.

BRIEF DESCRIPTION OF THE DRAWING(S)

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements shown.

FIG. 12 is an exploded view of an antenna housing and reflector assembly with an attached and externally exposed electronics module housing.

FIG. 13 is an enlarged cross-sectional view of a polymeric plug used for sealing the antenna tube and housing shown in FIG. 12.

FIG. 14 is a front elevational view of a first type of end cap for the antenna reflector assembly shown in FIG. 12.

FIG. 15 is a front elevational view of a second end cap for the antenna reflector assembly shown in FIG. 12.

FIG. 27 is a schematic view of a pile showing the connection between the top and tip sensor/gauge packages and the radio/electronics compartment.

FIG. 28 is a schematic view of a pile similar to FIG. 27, in which the pile includes a wire reservoir and guide tube to allow for connection to the embedded tip gauges for pilings which have the top cut off after driving.

FIG. 29 is a cross-sectional view through the piling taken along line 29-29 in FIG. 28.

DETAILED DESCRIPTION OF THE PREFERRED EMBODIMENT(S)

Figure 1:
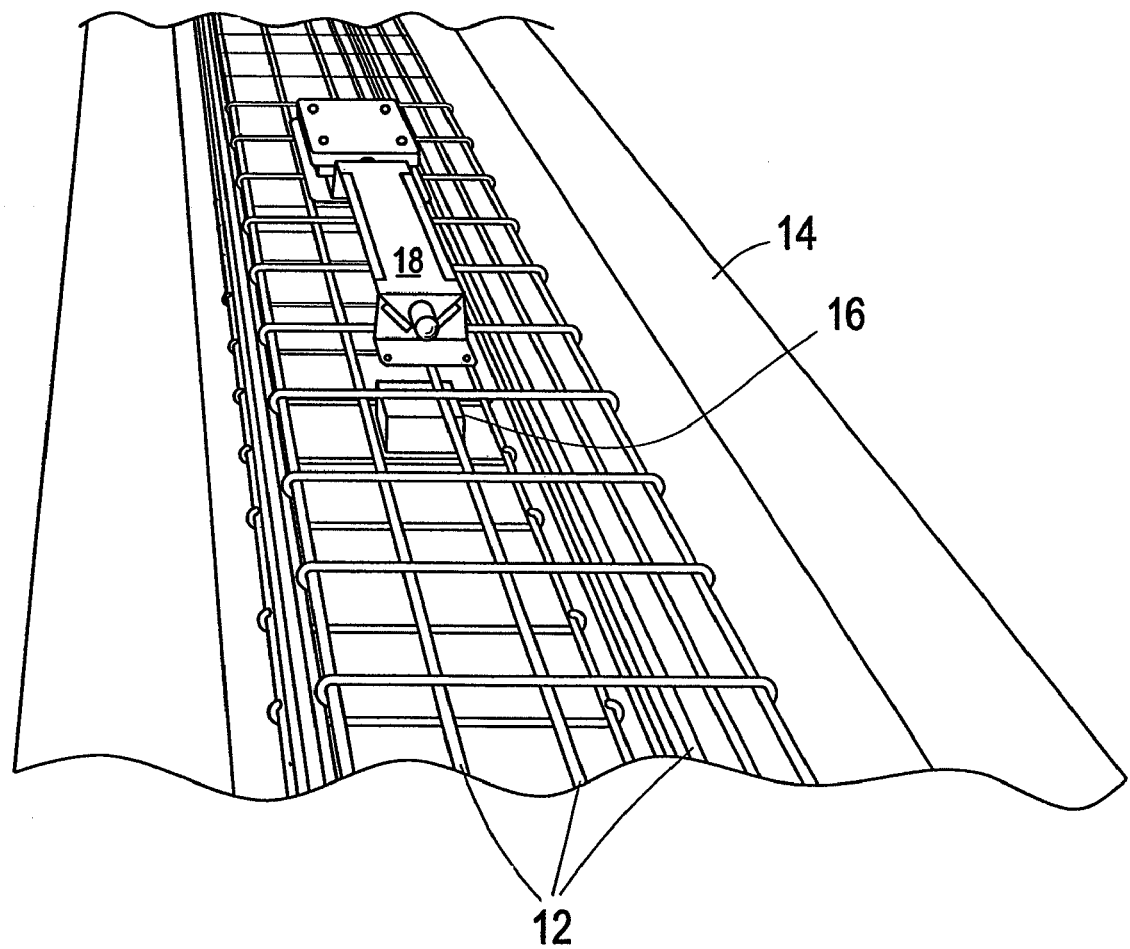
FIG. 1 is a perspective view showing strands in a piling form prior to casting concrete into the form in order to form the piling.

Certain terminology is used in the following description for convenience only and is not considered limiting. The words "lower", "upper", "left" and "right" designate directions in the drawings to which reference is made. As used herein, the recitation of "at least one of A, B and C" means any one of A, B or C or any combination thereof, where A, B and C represent the noted features of the invention. Additionally, the terms "a" and "one" are defined as including one or more of the referenced item unless specifically noted.

Referring to FIG. 1, strands 12 for a piling 10 are shown positioned in a piling form 14 prior to casting concrete in the form 14 in order to form the piling. Sensors 16 and an antenna assembly 18 for transmitting data from the piling during or after installation are shown connected to or suspended from or above the strands 12, preferably using cable ties or similar holding devices. Sensors and antennas are preferably used for monitoring of the pilings using a direct wireless data transfer of data being gathered by the sensors embedded in the pilings as described in detail below, for installation and/or lifetime monitoring of the piling as well as also possibly for storing pile data.

Figure 2:
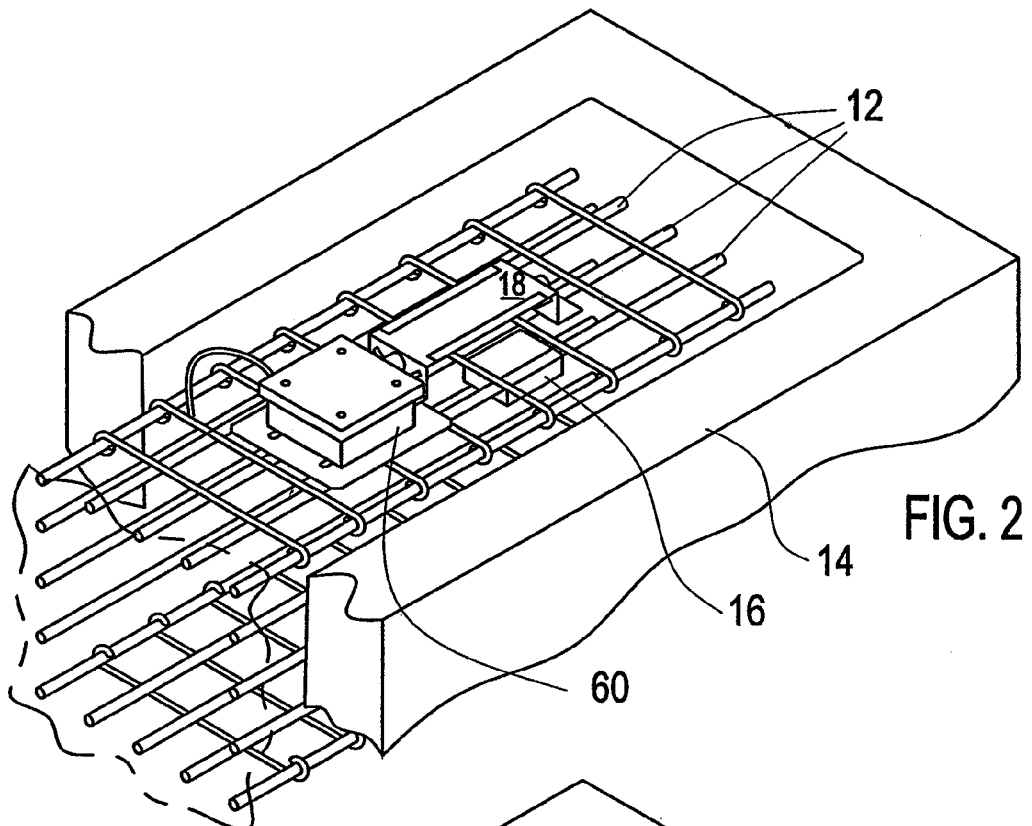
FIG. 2 is an enlarged perspective view similar to FIG. 1

FIG. 2 shows an enlarged view of a preferred antenna/radio assembly 60 temporarily located lying on top of the pile strands 12, which will float in the concrete that is cast in the form so that a top surface of the antenna/radio assembly 60 is located on a surface of the pile. Additionally, the sensors 16 are attached to a preferred suspension assembly as explained in further detail below in order to position the sensors 16 between the piling strands 12.

Figure 3:
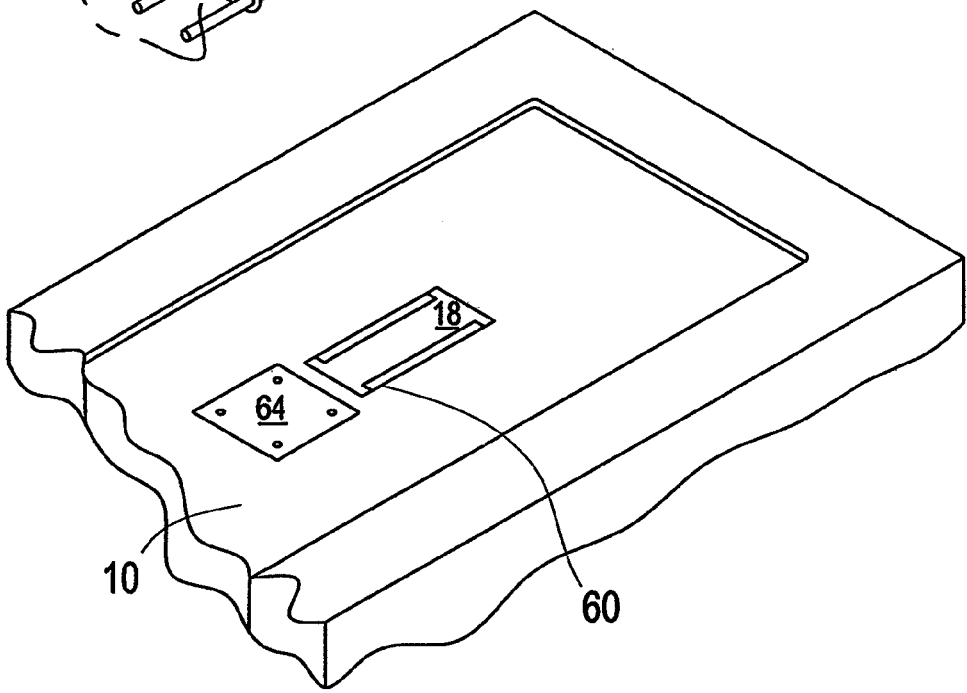
FIG. 3 is a perspective view showing the piling form after the concrete has been cast into the form.

FIG. 3 shows the piling 10 cast in the form 14 after the concrete has been poured. The surface of the antenna 18 remains exposed for signal transmission before, during and/or after the pile drive. Also, the cover 64 of the antenna/radio assembly 60 remains exposed. It is also possible to remove the antenna 18 and incorporate the antenna into the cover 64 of the electronics module housing 61, as explained in detail below.

Figure 4:
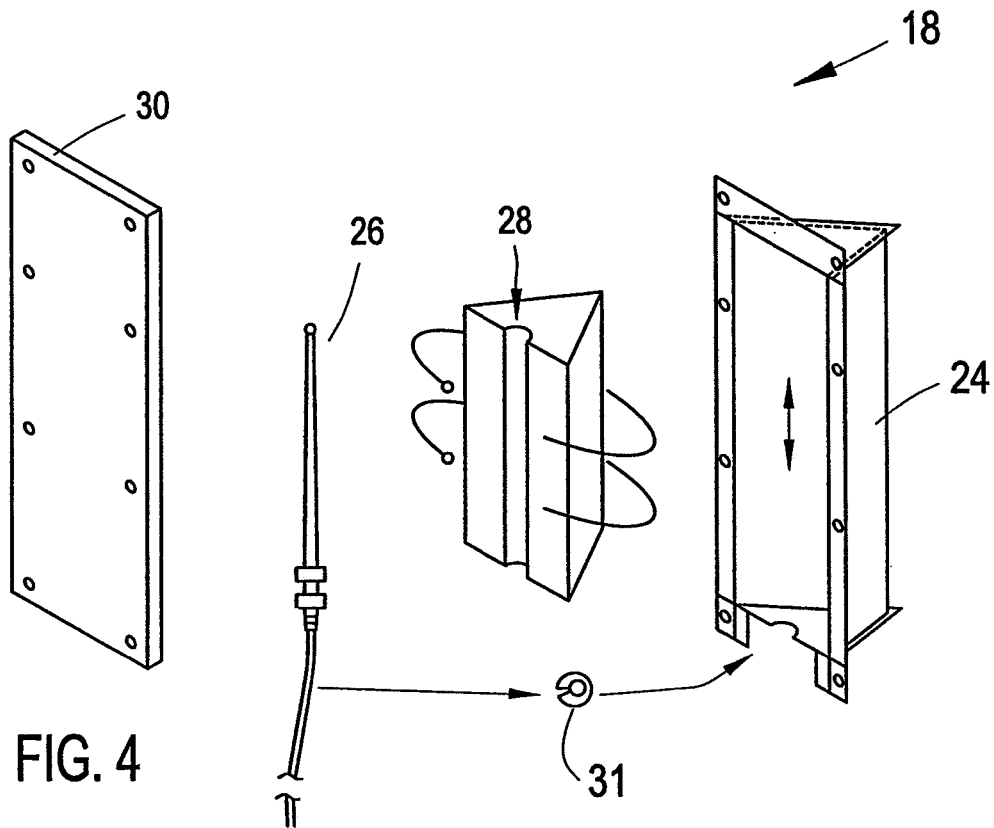
FIG. 4 is an exploded view of a first embodiment of an antenna assembly in accordance with a first embodiment of the present invention.
Figure 5:
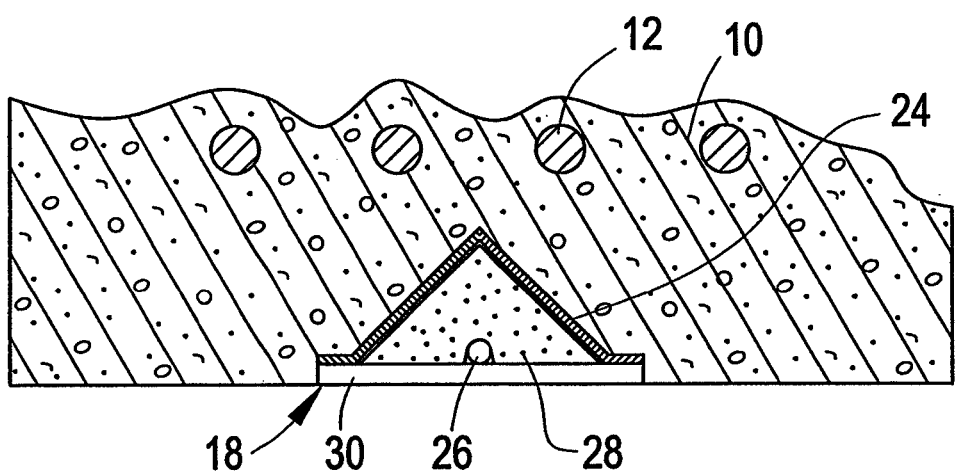
FIG. 5 is a cross-sectional view of the antenna of FIG. 4 shown embedded in a side of a concrete structure, such as a piling.

A first embodiment of an antenna assembly 18 according to the present invention is shown in FIGS. 4 and 5. The antenna assembly 18 is flush mounted in the side of a concrete structure, such as the piling 10, shown in FIG. 3, during fabrication. It is necessary to ensure that the antenna is decoupled from the surrounding concrete of the piling 10. This is achieved by providing a corner reflector 24, preferably made of metal, such as steel or aluminum, or may be made from plastic with an electrically conductive coating. While prior corner antennas have been used in other applications to provide gain, in the present case it is used in an unconventional manner to provide isolation of the antenna from the surrounding concrete structure 12 in which it is embedded. In a typical corner reflector application, the reflector is placed a ½ wave length away from the antenna such that the reflected wave will add in phase and provide gain. Due to the depth restriction in the present application based on the structural reinforcements in the concrete, the metal surface of the corner reflector 24 is only placed far enough from the antenna so as to minimize the detuning effects to the antenna (resulting in impedance mismatch losses), and not too far away so as to minimize the destructive interference caused by the reflected wave. In one application, a distance of 2.1 inches is preferred for a reference wavelength of 916 MHz, providing a spacing of approximately ⅙ of a wave.

In another embodiment of the invention with a shorter wavelength/higher frequency (for example, 2.4 GHz), a smaller overall geometry of the embedded antenna assembly is provided with only a spacing of about 1 inch being necessary.

Still with reference to FIGS. 4 and 5, an antenna 26 is held in position relative to the back metalized reflector with an open cell foam block 28 or other similar non-moisture absorbing or holding spacer. Preferably, a cover plate 30 made of an RF transparent material at the frequency of interest is installed over the antenna 26. Preferably, the cover is flush with the surface of the concrete structure 12, as shown in FIG. 3. A grommet 31 is preferably placed around the wire or coax cable extending from the antenna 26. The entire assembly 18 is preferably assembled in a water tight manner.

Figure 6:
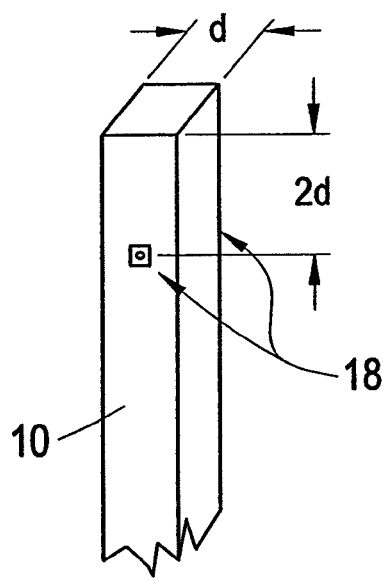
FIG. 6 is a perspective view showing the location of opposing antennas located on the top of a pile.

Referring to FIG. 6, a preferred placement of the antenna 18 on opposing faces at the top end of the pile 10 is shown. Preferably, the antenna assembly 18 is located $2d$ down from the top where d is a width of the pile 10. The sensors 16 are preferably also placed at a location $2d$ from the top and additional tip sensors are placed $2d$ from the pile tip, as noted in detail below. However, the sensors are located in the middle/core of the pile cross-section.

Figure 7:
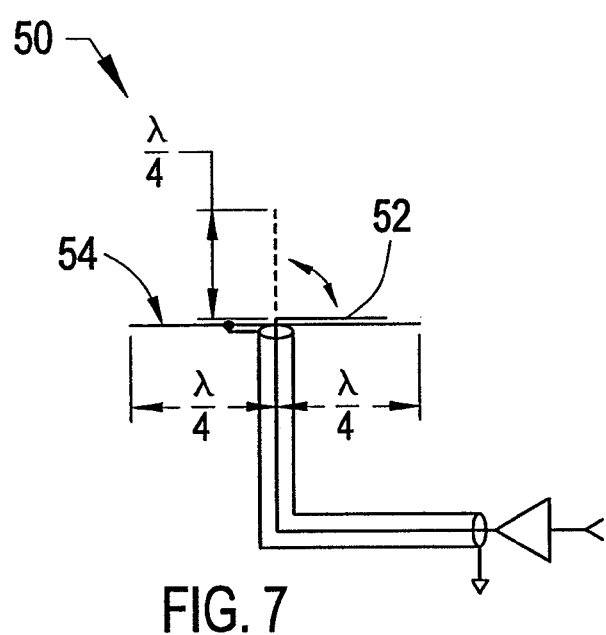
FIG. 7 is a side view of a deployable antenna assembly that is flush mounted to the surface of a concrete structure.
Figure 8:
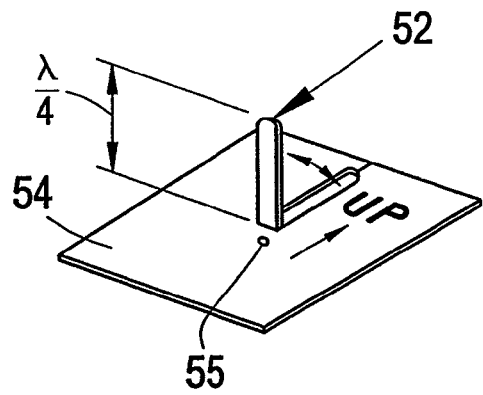
FIG. 8 is a perspective view of the antenna of FIG. 7.

Referring to FIGS. 7 and 8, in another embodiment of the invention, a single (or multiple) retractable, spring-loaded antenna assemblies 50 are provided. The antenna 52 remains flush with the pile surface during manufacturing and transportation of the pile. The antenna assembly(s) 50 have the antenna 52 extend to a deployed position only after either a significant vertical blow, such as from an actual pile hammer blow, or after a control command is received and actuates a solenoid driven release. An electrically conductive ground plane 54, preferably made of metal or an electrically conductive material coated on an insulating substrate, is mounted flush to the surface of the concrete structure, and in effect sits on the surface like the cover 30 until the antenna is deployed, and thereupon acts as a part of the antenna structure. The length of the antenna 52 is preferably ¼λ, and the ground plane 54 has dimensions of approximately λ/2 and could be round or square with a diameter or side length of approximately λ/2. While this arrangement is preferred, other arrangements are possible.

Alternatively, or in addition to the remote release, a manual push button override 55 is provided in case the automatic extension attempts for the antenna assembly 50 fail. This can be in the form of a small opening located in the ground plane 54 to allow a user to insert a rod or pin and release a catch holding the antenna 52 in the stowed position.

Figure 9:
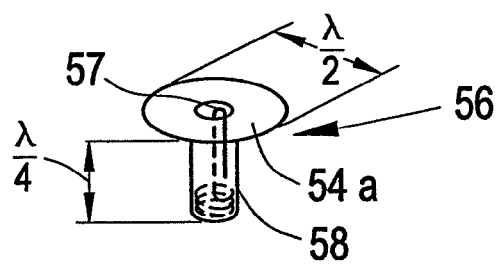
FIG. 9 is a perspective view of an alternate embodiment of a site deployable antenna according to the invention.

Once the proper magnitude blow or control command is received, the antenna(s) 52 extends orthogonal from the concrete surface. This is easily achieved through a hinge-mounted antenna 52, as shown in FIG. 8. The blow or control activated solenoid or plunger releases a catch, and the antenna rotates outwardly driven by the force of a circumferential force coil spring or a compression spring (not shown). Alternatively, as shown in FIG. 9, the assembly 56 can include an antenna 57 located in an electrically non-conductive sleeve 58 that extends generally orthogonally to the surface of the electrically conductive ground plane 54a located on the surface of the concrete structure, and upon activation of a release catch, either through a detected blow or through a control signal as described above, the catch is released resulting in the antenna 57 springing outwardly from the sleeve 58 to an extended position above the ground plane 54a.

If an antenna(s) hits grade (water or ground) during installation, internal sensing circuitry will switch transmission of data to an above-grade antenna or internal transceiver as in the case of a spliced pile or allow direct connection via a jack to export data, as discussed in detail below.

Figure 10:
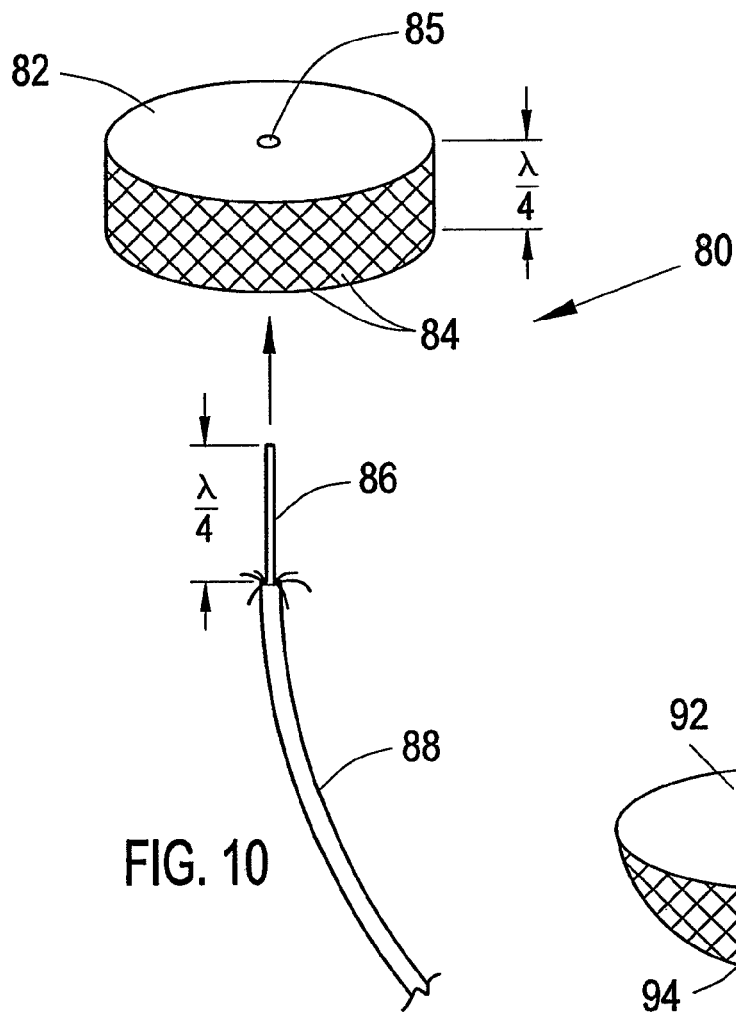
FIG. 10 is a perspective view, partially disassembled, of a reflector used to form another antenna assembly according to the invention.
Figure 11:
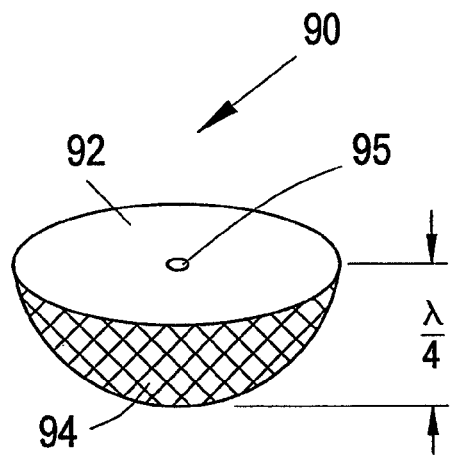
FIG. 11 is a perspective view showing a second reflector assembly, partially disassembled, in accordance with the present invention.

Referring to FIGS. 10 and 11, two additional alternative embodiments of antenna assemblies 80, 90 are shown. These antenna assemblies are constructed in a very cost effective manner, and use of a low loss and low dielectric material plug 82, 92 having a thickness of λ/4 and preferably a diameter greater than or equal to λ/2. The plug can be made of plastic or any suitable material meeting the requirements set forth above, and is preferably cylindrical (FIG. 10), hemispherical or parabolic (FIG. 11). The sides and bottom are covered with an electrically conductive coating 84, 94, such as metalized foil or any other suitable material. An externally sealed center opening 85, 95 is provided through which the center wire 86, 96 of a coax cable 88, 98 extends to a length of λ/4. The ground braid of the cable 88, 98 is soldered or otherwise connected to the electrically conductive coating 84, 94 in the area of the center opening 86, 96 where it extends through the bottom of the plug 82, 92. The top surface of the plug 82, 92 acts as a cover and is installed flush with the surface of the concrete structure during fabrication in order to provide a low cost antenna.

Referring to FIGS. 12 through 15, a preferred embodiment of the upper antenna/radio assembly 60 is shown in detail. The antenna assembly 60 preferably includes a reflector assembly 65 having a reflector body 66 formed from a bent-up metallic sheet, preferably formed into a V-shape, with end caps 68 and 70, shown in FIGS. 14 and 15, attached to the ends thereof. Preferably, the reflector assembly 65 is formed from metallic materials, such as aluminum or stainless steel. However, other suitable metallic materials may be utilized or a polymeric material having a metallic coating would also be suitable. A protective cover 72 formed of an RF transparent material at the desired frequency is provided. The cover 72 is required during manufacture of the piling in order to keep concrete out of the antenna assembly 60 during casting, and can be removed after the concrete is set, if desired. In a preferred embodiment, this is formed of heavy card stock/cardboard or a polymeric material having a thickness of above 0.02 inches and can be adhered, taped or otherwise sealed onto the reflector assembly 65.

The antenna assembly 60 further includes the housing 61 for wiring and electronic components associated with the antenna 76 as well as a radio module for transmission of a data signal. The antenna 76 is preferably located within an antenna tube 78 formed of a polymeric material, such as PVC, that is connected in a water tight manner to the housing 61, preferably using a coupling 69 that extends from the housing 61 and a plug 79 inserted from inside the housing 61 into the coupling 69 and around the antenna base, shown in detail in FIG. 13. The plug 79 is preferably sealed or glued within the housing 61, as indicated at 81. The reflector assembly 65 is installed over the antenna tube 78 such that the first end cap 68 is up against the housing 61. A tube end cap 83 is used to seal the end of the antenna tube 78 after the antenna 76 is installed. Water tight connectors 91 can be inserted into opening(s) in the sides of the housing 61 in order to provide water tight entry and exit points for wiring, cables or the like used for data signal transmission and/or power transmission to the various elements of the sensing system located within the piling 10. Additionally, a buoyancy compensation plate 87 is preferably connected to the bottom of the housing 61 with, for example rivets, to the provided flanges or by any other suitable connection, such as clips, adhesive, cable ties or the like. The buoyancy compensation plate 87 is sized so that a sufficient amount of concrete is located thereon to counteract the buoyancy of the antenna assembly 60 so that it is maintained in a floating position above the piling strands with the cover 72 generally flush with the piling surface.

Preferably the housing 61, the coupling 69, the plug 79, the antenna tube 78, the anti-buoyancy plate 87 and the end cap 83 are all made of PVC or a similar polymeric material and can be assembled and adhered together in a simple and efficient manner. The cover 72 for the reflector assembly 65 is preferably positioned within the piling form 14 so that it is maintained along and forms a portion of the outer surface of the piling. Additionally, preferably an access cover 64 is provided for the housing 61, and is also located at the surface of the piling in order to allow access to the wiring, cables, battery, diagnostic support, and/or electronic components located therein after the piling is formed.

Figure 16:
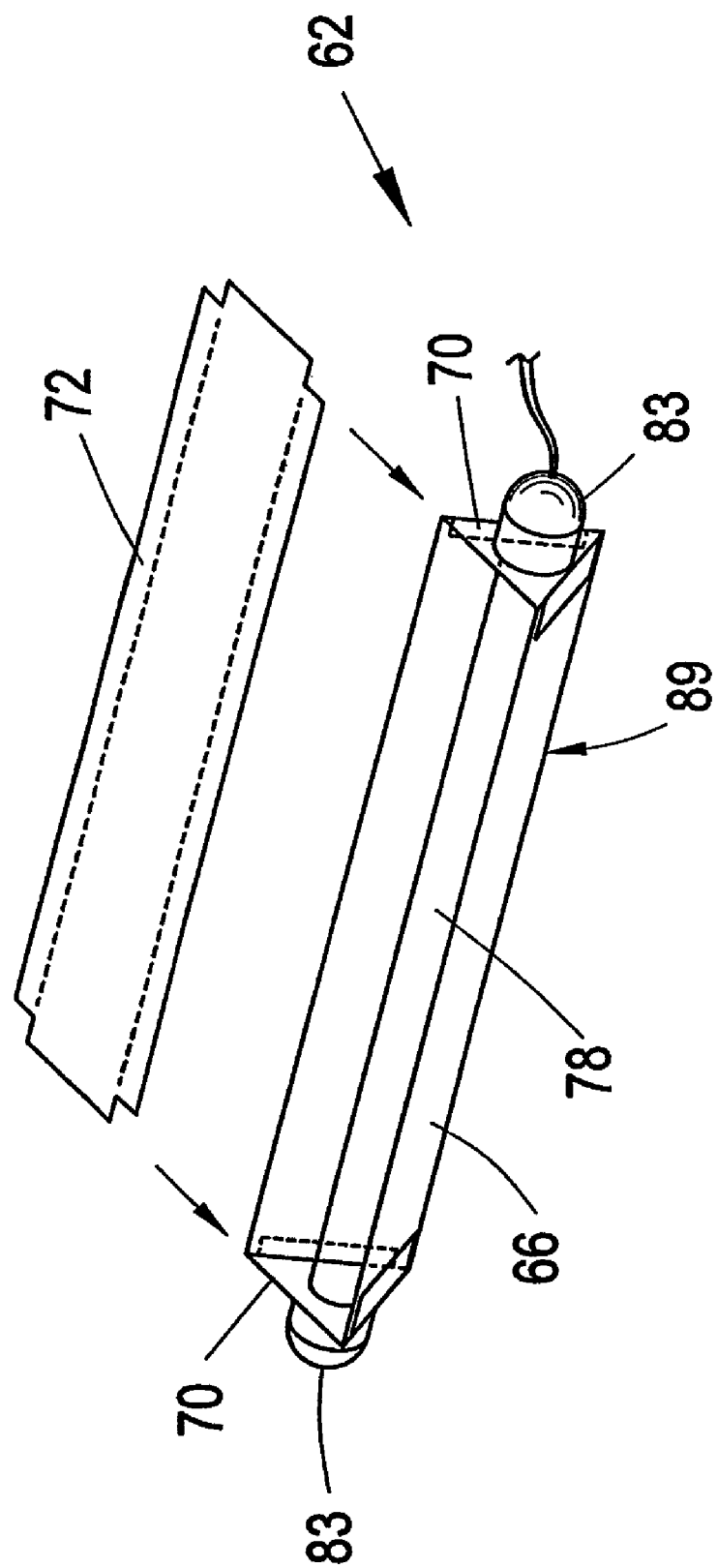
FIG. 16 is a perspective view of another antenna assembly according to the invention, similar to that shown in FIG. 12, without the electronics module housing.

Referring to FIG. 16, the reflector assembly 89 for the second antenna assembly 62 is shown and includes the cover 72 as well as the preferably V-shaped reflector body 66. Two reflector end caps 70 are utilized to close off the ends of the reflector assembly 89 and the antenna 76 within the antenna tube 78 are installed therein. Once the antenna is installed within the tube 78, the ends are sealed in a water tight manner utilizing tube end caps 83 or similar type end caps so that only the antenna cable extends out from one end of the reflector assembly 89 in order to form the second antenna assembly 62.

Figure 17:
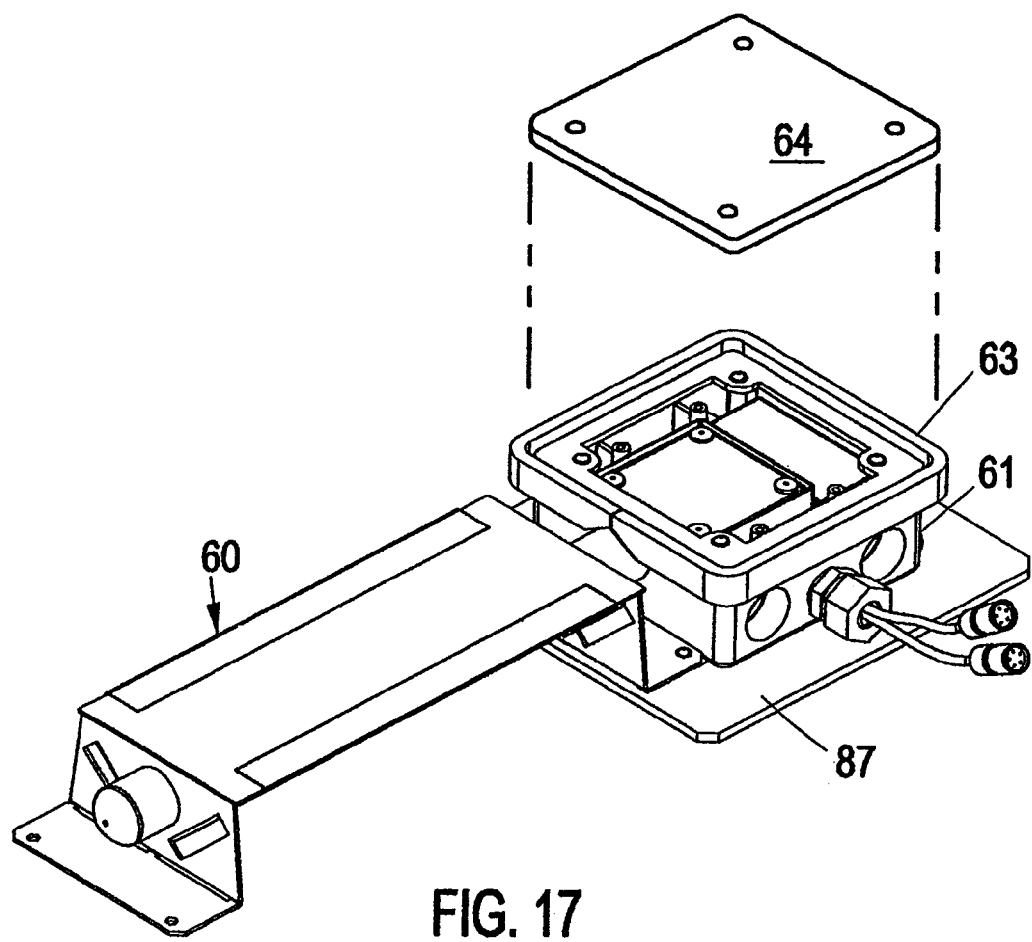
FIG. 17 is a perspective view of an antenna assembly similar to that shown in FIG. 12, with a release gasket located around the electronics module housing cover.
Figure 18:
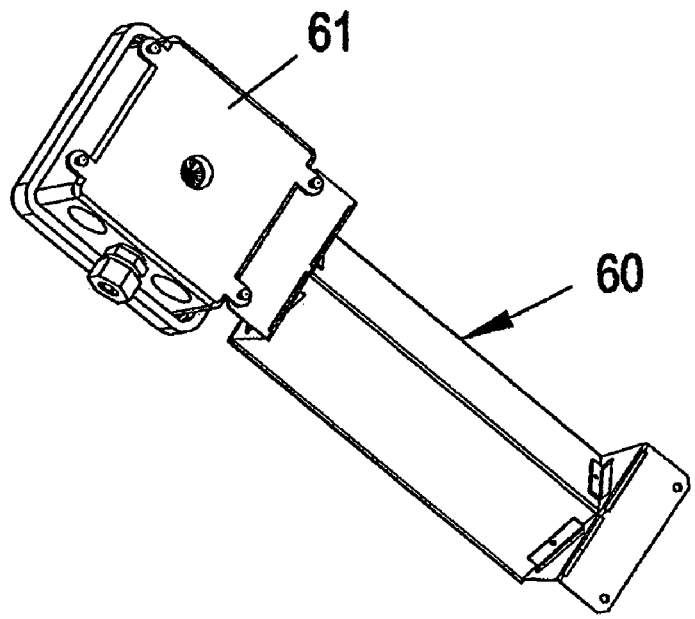
FIG. 18 is a rear perspective view of the antenna assembly shown in FIG. 17.

Referring to FIGS. 17 and 18, the preferred antenna/radio assembly 60 is shown with an improvement for installation. In order to allow removal of the cover 64, a foam or rubber sleeve 63 is installed around the top of the housing 61, as shown in FIG. 17, and extends up past the lip of the cover 64. This prevents the concrete that is used to form the pile 10 from locking the cover 64 in position, and the sleeve 63 is preferably removed after the concrete is set to provide an air gap to allow removal of the cover 64. Alternatively, the sleeve 63 can remain and act as a seal to prevent the ingress and settling of moisture.

A plurality of individually switchable and uniquely identified antennas are preferably embedded in the concrete piling structure, preferably including one antenna assembly 60 with an attached radio module in the housing 61, and possibly one or more of the antenna assemblies 62 or other types of the antenna assemblies identified above. The antennas are enabled, preferably automatically, in a round robin fashion to identify with a receiving system which antenna position provides the best signal strength and subsequently the highest data bandwidth capabilities based on the physical position of the receiving system. Only this antenna (position) is then selected and enabled for all subsequent data correspondence. In order to optimize performance, power is not routed to the unused antenna positions during data acquisition. It is possible that if during data acquisition, the signal from the selected antenna is lost, the system can try to automatically establish contact with one of the remaining antennas.

The antenna selection criteria is preferably based on a combination of the received signal strength indicator signal (RSSI), link quality, and calculated test signal transmission bandwidth. The specific protocol used to select and enable the antenna can be selected based on the particular systems utilized and application. However, generally only the antenna with the best transmission performance is selected for use and powered. Once selected, full system power is sent to the selected antenna to extend the system battery life while providing the best signal strength and the highest bandwidth. Also, because the antenna structure is exposed on the face of the piling, the use of multiple antennas provides redundancy and recovery options in the event of damage to one antenna.

Figure 19:
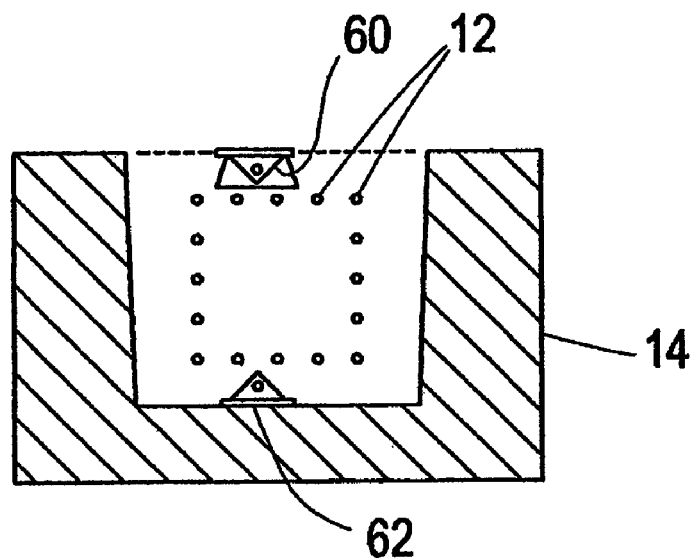
FIG. 19 is a cross sectional view through a piling form showing the opposite positioning of antenna assemblies according to the invention in the piling form.

Referring now to FIG. 19, antenna assemblies 60, 62 are shown positioned within the piling form 14. The upper antenna assembly 60 is preferably floating in the concrete above the strands 12 to prevent any sources of water ingress from reaching the strand skeleton after manufacture. The lower antenna 62 may be placed at the bottom of the form flush with the bottom surface, and is held in position by the weight of the concrete being cast. Other types of the antenna assemblies described above could also be utilized. It is also possible to locate the antenna assemblies on opposing sidewalls of the piling form 14.

One problem encountered with the installation of the sensors shown in FIGS. 1-3 is that during pouring of the concrete and subsequent settling using a vibrator or other means, the potential for damage to the sensors was increased due to the horizontal mounting of the sensors on or between the strands 12, presenting a large profile through and over which concrete must be poured and/or tamped.

Figure 20:
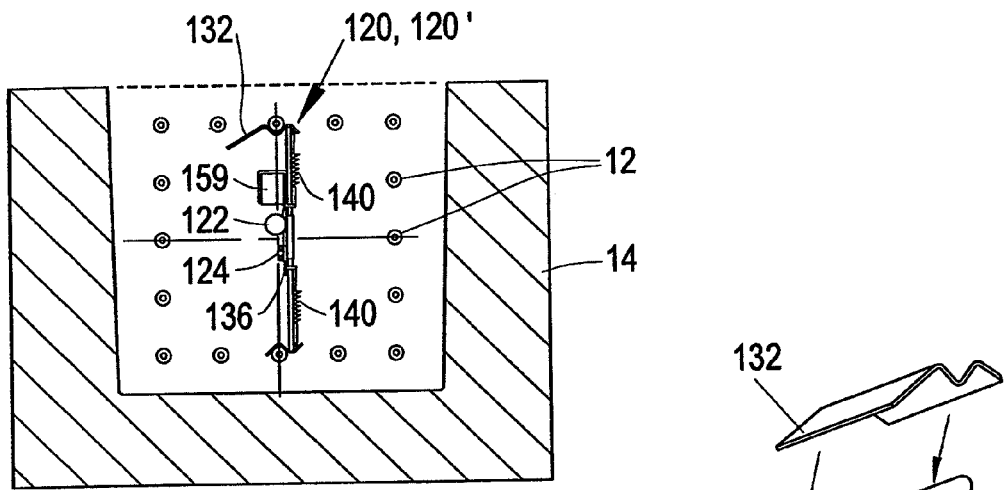
FIG. 20 is a cross-sectional view through the piling form showing the strands and a U-Bar suspension assembly according to the invention for vertical mounting of gauges in the piling.

As shown in FIG. 20, in accordance with the present invention a U-Bar suspension assembly 120, 120' is preferably installed generally vertically in the piling form 14 in order to facilitate fast, accurate and repeatable positioning of the sensors located thereon. Preferably, this includes an accelerometer 122 and a strain gauge 124, which must be positioned cross-sectionally within the pile core. The U-Bar suspension assembly 120, 120' is preferably spring loaded and allows repeatable positioning of the sensors within a center of the core area of the piling form 14 without the need for hand measurements while maintaining the accelerometer in a position orthogonal to the pile length in order to allow accurate acceleration measurements during subsequent driving of the pile, and also maintaining the strain gauge in a position parallel to a longitudinal axis of the pile to ensure accurate strain measurements.

Figure 21:
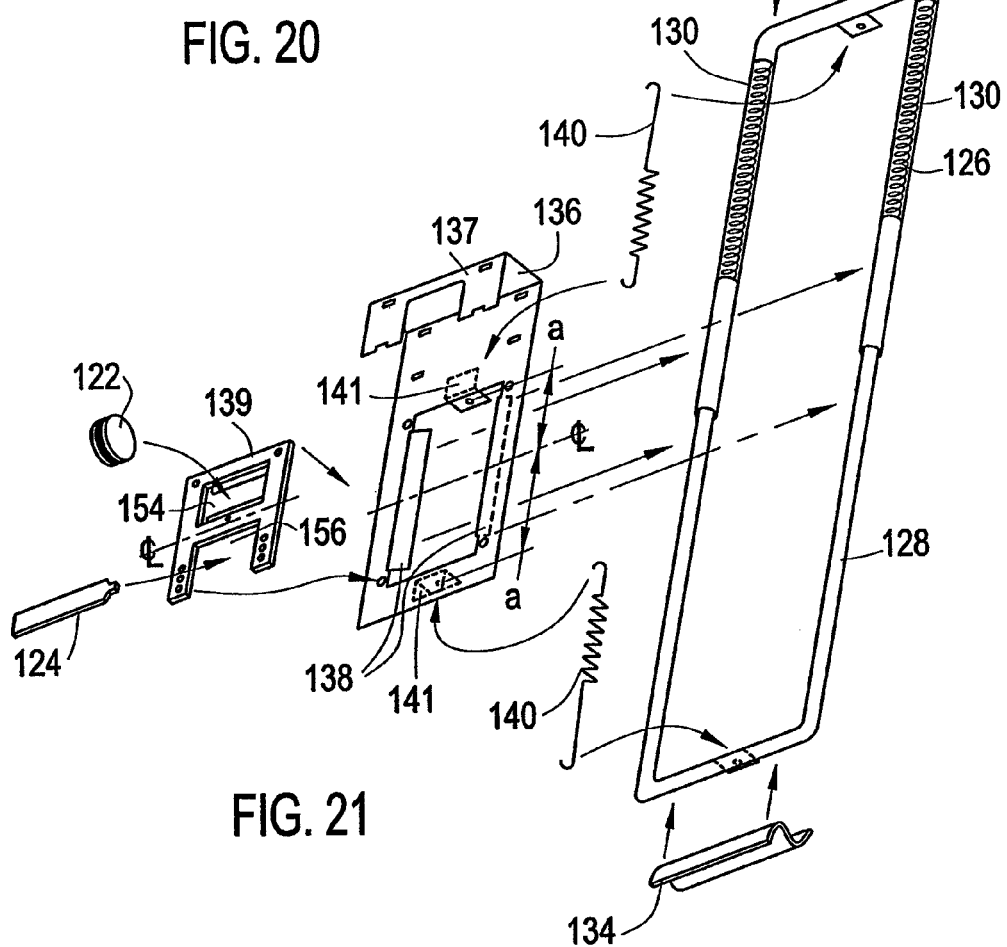
FIG. 21 is an exploded perspective view of the U-Bar suspension assembly.
Figure 22:
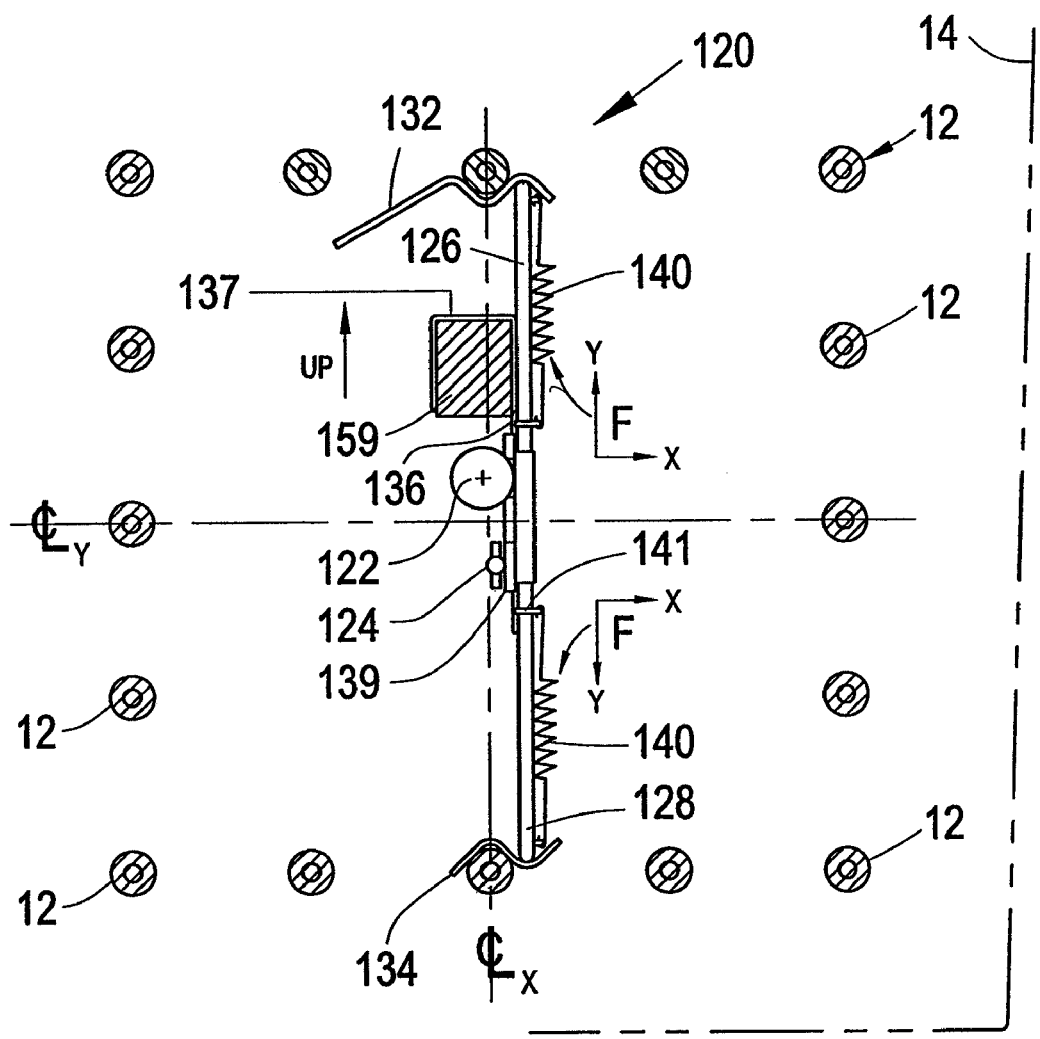
FIG. 22 is a side elevational view, shown partially schematically, of the assembled U-Bar suspension assembly shown with a strain gauge, an accelerometer and an electronics module mounted thereon.

Referring to FIGS. 21 and 22, a first embodiment of the U-Bar suspension assembly 120 will be described in detail. The U-Bar suspension assembly 120 includes upper and lower U-shaped frames 126, 128. The legs of the lower U-shaped frame 128 are slidable within the legs of the upper U-shaped frame 126. Springs 130 are located within the legs of the upper U-shaped frame 126 and bias the upper U-shaped frame 126 away from the lower U-shaped frame 128. A combined upper shield/hook 132 and one or more lower hooks 134 are each attached to the base of the upper and lower U-shaped frames 126, 128, respectively. The shield/hook 132 and hook(s) 134 can be made of any suitable material that avoids galvanic corrosion and may have any suitable shape which is sufficient to engage the strands 12 when the U-Bar assembly 120 is installed in a generally vertical orientation in the piling form 14, as shown in FIG. 22. The upper shield/hook 132 is preferably wide enough to protect the gauge/sensor arrangement from damage during casting of the concrete and subsequent vibratory settling/tamping.

For installation, the U-Bar suspension assembly 120 can be inserted between the strands 12 with the lower hook(s) 134 engaged on a lower strand 12. The U-Bar suspension assembly 120 is then compressed by pressing the upper U-frame downwardly against the force of springs 130 so that the legs of the lower U-frame 128 are telescopically received within the legs of the upper U-frame 126. Upon releasing force on the upper U-frame 126, the upper and lower U-frames 126, 128 are biased away from one another by the springs 130 and the hook portion of the upper shield/hook 132 can engage against the underside of an upper strand 12 within the piling form 14.

Referring again to FIGS. 21 and 22, the U-bar suspension assembly 120 further includes a carrier sled 136 connected thereto. The carrier sled 136 preferably includes guide flanges 138 which contact the legs of the upper and lower U-shaped frames 126, 128 in order to position the mounting platform. An upper portion of the carrier sled 136 preferably includes an extension 137 that is bent in a generally U-shape in order to hold and protect an electronics module 159, shown in FIG. 22. Alternatively, this can be a separate piece or part of the electronics module housing.

Centering springs 140 are preferably provided and have a first end connected to the upper U-shaped frame 126 and the lower U-shaped frame 128, respectively. The second ends of the centering springs 140 are connected to brackets 141 on the upper and lower sides of the carrier sled 136 and bias the carrier sled 136 to a generally centered position regardless of the distance between the hooks 132, 134 in the installed position on the strands 12. The brackets 141 are spaced so that the gauge/sensor assembly will be approximately centered in the piling, preferably by equal spacing "a" from a center line of the mounting position of the sensor/gauge assembly. As shown in FIG. 22, the force vectors for the centering springs 140 have primary Y force components. However, based on the mounting arrangement, there is also the possibility of providing an X force component that holds the carrier sled 136 against the U-shaped frame members 126, 128. The centering springs 140 ensure that the carrier sled 136 is in a repeatable, centered position upon installation without the need for an installer to reach down between the strands and measure and adjust the position of the carrier sled 136. The centering springs 140 have a lower spring constant than the springs 130. Once the suspension assembly is in position, the carrier sled 136 is clamped and/or held in the centered position using wire ties, hose clamps, thumb screws or other similar devices. This prevents concrete and/or the subsequent vibration/settling from moving the carrier sled 136 from the spring equilibrium position.

Alternatively, other spring arrangements can be utilized, or the centering springs 140 can be omitted and the mounting platform can be installed on the U-Bar suspension assembly 120 by cable ties, bent wire, or other suitable fasteners, such as those mentioned above.

A mounting plate 139 is connected to the carrier sled 136, preferably with cable ties, wire ties or the like. The mounting plate 139 registers in position on the carrier sled 136, preferably using alignment holes, tabs or other similar measures. The accelerometer assembly 122 is preferably attached to the mounting plate 139 with cable ties or other suitable types of connectors, such as mechanical fasteners, epoxy or any other suitable means. Alternatively, the mounting plate 139 can be omitted and its mounting features incorporated onto the carrier sled 136.

Figure 23:
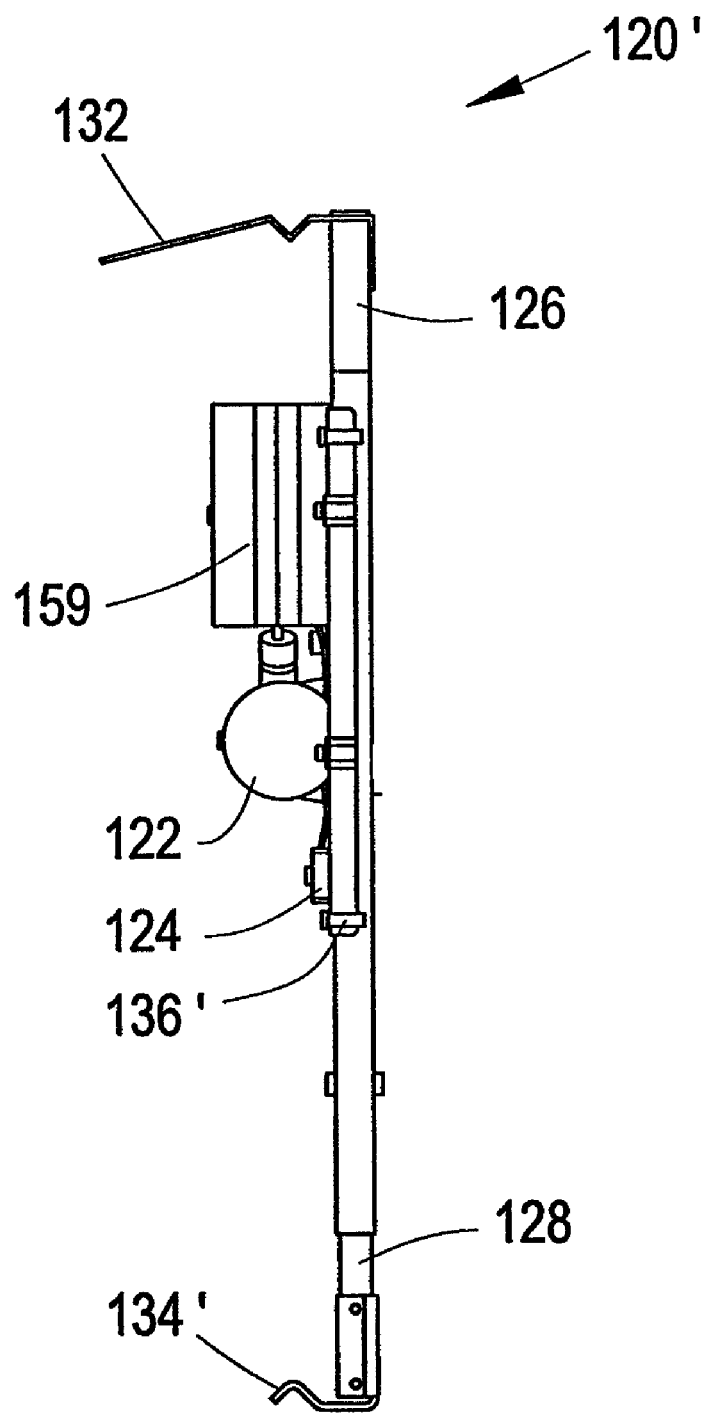
FIG. 23 is a side elevational view similar to FIG. 22 of another embodiment of a U-Bar suspension assembly with the strain gauge, accelerometer and electronics module.
Figure 24:
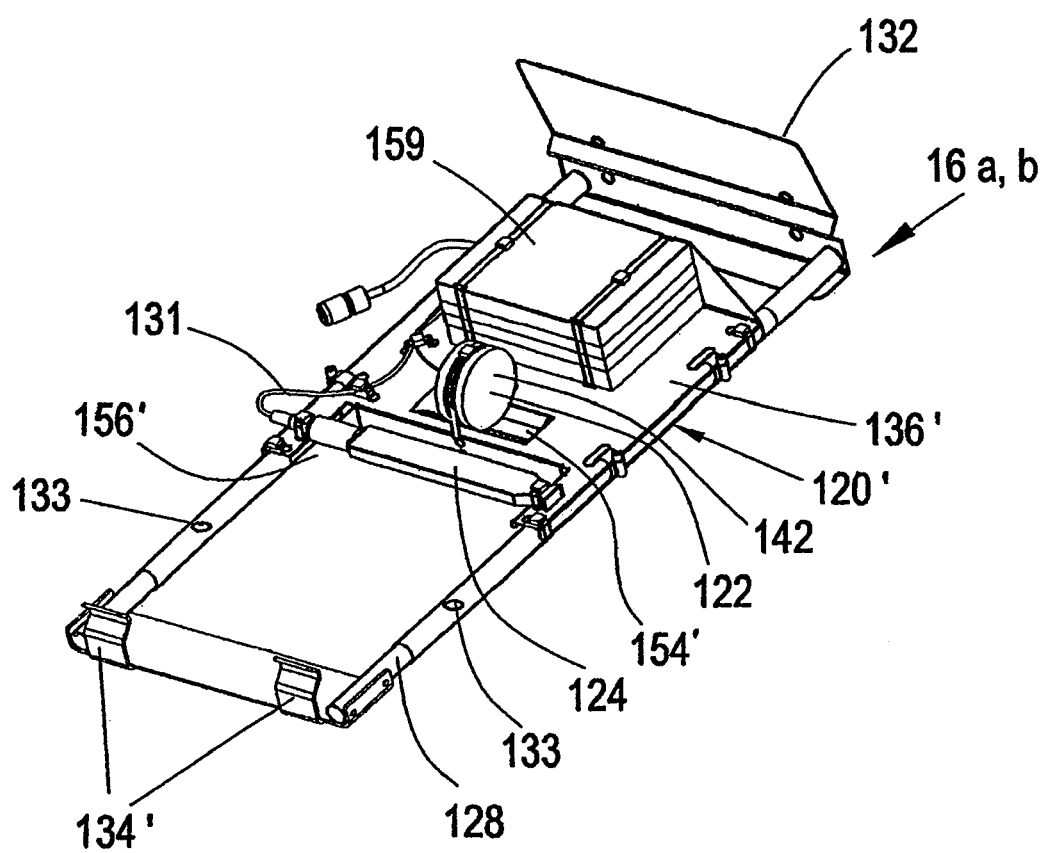
FIG. 24 is a perspective view of the electronics and sensor mounting on the center section of the U-bar suspension assembly of FIG. 23.
Figure 25:
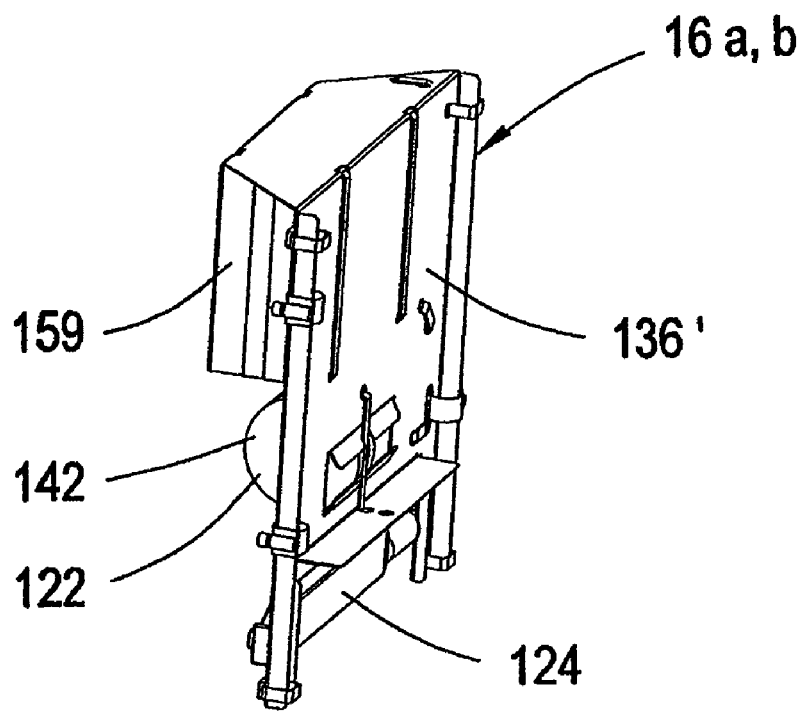
FIG. 25 is a rear perspective view showing the sensor mounting relative to the U-bar suspension assembly of FIG. 24.

Referring to FIGS. 23 and 24, a second embodiment of the U-bar suspension assembly 120' is shown. The second embodiment 120' is similar to the embodiment 120, except the need for the springs 130 has been eliminated, and the mounting plate 139 is eliminated with its function being incorporated in one piece with the carrier sled 136'. In the U-bar suspension assembly 120', the U-frames 126, 128 are slidable together and apart in the same manner as discussed above. However, the lower U-frame 128 includes a series of holes in the legs which can be aligned with holes in the legs of the upper U-frame 126 and pinned together using pins 133, which can be pins, bolts, rivets or any other suitable fasteners. The U-frames 126, 128 are adjusted for the particular strand 12 spacing for a pile 10 to be formed. The pins 133 are then installed. The bottom hooks 134' are formed of spring steel or another suitable resilient material. During installation, the U-bar suspension assembly 120' is inserted between the strands 12 and the lower spring hooks 134' engage a lower strand. The spring hooks 134' elastically deflect in order to allow the upper hook 132 to be inserted under the desired upper strand 12 in the form 14, and then resiliently bias the upper hook 132 into engagement with the upper strand. The strands themselves also provide some resiliency and can be sprung apart to allow installation of the U-bar suspension assembly. The holes in the legs of the lower U-frame 128 can be positioned in the appropriate locations for known standard strand locations for a number of known piling sizes. The carrier sled 136' with the attached gauges and sensors can be connected to the U-frames 126, 128 in a centered location using cable ties, clamps, rivets or any other suitable fasteners.

Figure 26:
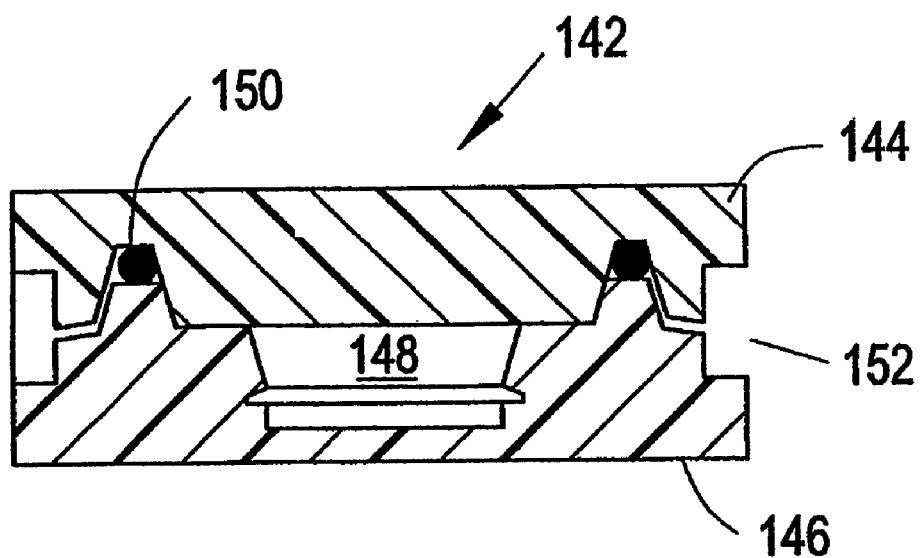
FIG. 26 is a cross-sectional view of a water tight housing for the accelerometer.

Preferably, the accelerometer assembly 122 preferably includes a housing 142, as shown in detail in FIG. 26, which maintains a water tight cavity in which the physical accelerometer device is held. The housing 142 is preferably made of a top housing part 144 and a bottom housing part 146 which define a cavity 148 for the physical accelerometer device therein. An O-ring 150 is located in a circumferential groove in the upper housing part 144. Once the physical accelerometer device is installed within the cavity 148, the top and bottom housing parts 144, 146 are assembled, preferably using an adhesive to hold the parts 144, 146 together. The top and bottom housing parts 144, 146 for the accelerometer housing 142 are preferably made from a polymeric material, such as a low cost polycarbonate. A channel 152 is preferably formed around the periphery of the housing 142 which allows for the physical alignment and mounting on the carrier sled 136' or the mounting plate 139, if provided separately, using a cable tie received within the channel 152, as shown in FIGS. 22-25.

As shown in FIG. 21, preferably an opening 154 is located in the mounting plate 139 in which the accelerometer housing 142 is secured. The opening 154 has V-shaped sidewalls for registration/alignment so that the accelerometer housing 142 is held firmly and accurately in position by the peripheral circumferential edges of the housing 142 being in registration with V-shaped walls. Slots are preferably provided in the mounting plate 139 for the cable ties to extend through for attachment of the accelerometer. The opening 154 also allows the concrete used for the piling to form around the accelerometer assembly 122 in its housing 142 in order to ensure that accurate data is collected by the accelerometer. Alternatively, as shown in FIG. 24, the same type of opening 154' is located directly in the carrier sled 136' to allow mounting of the accelerometer assembly 122 in the same manner.

The strain gauge 124 is preferably also installed on the carrier sled 136' or the mounting plate 139, if provided as a separate part for pre-assembly, using cable ties. As shown in FIG. 21, an opening 156 is preferably provided through the mounting plate 139 in the area of the strain gauge 124 so that the concrete used for the piling can be formed around the strain gauge 124 in order to ensure that accurate data is collected by the strain gauge 124. A similar opening 156' is also provided directly in the carrier sled 136' in the embodiment shown in FIGS. 23 and 24.

An electronics module 159 for the strain gauge 124 and the accelerometer is also preferably attached to the carrier sled 136, 136', as shown in FIGS. 22 and 24. Alternatively, this can be positioned elsewhere in the piling form 14.

The mounting plate 139 is preferably formed from a polymeric material, such as Lexan™ or any other suitable polymeric material. The upper and lower U-shaped frames 126, 128 are preferably made of steel rod, tube or other structure and the hooks 132, 134 are preferably also made of a compatible metallic material, preferably steel, and connected to the upper and lower U-shaped frames 126, 128 via welding, riveting or other suitable means. The hook 134' is made of spring steel or a suitable resilient material, as discussed above. The carrier sled 136, 136' is preferably made of a compatible metallic material, such as steel.

Utilizing the U-Bar suspension assembly 120, 120' allows quick and easy installation in a consistent and repeatable manner relative to the piling strands 12 of the sensors such as a strain gauge 124 and accelerometer assembly 122 while maintaining a precise alignment and positioning so that the accelerometer is orthogonal to a length of and within the core of the piling being formed, and the strain gauge 124 extends axially, parallel to a length of and within the core of the piling being formed. The U-bar assembly 120, 120' is designed to provide for accurate mechanical registration of the gauge/sensor assembly on the sled 136 with the precisely located strands 12 in the piling form 14 based on the location of the strands in order to ensure accurate and repeatable placement of the gauge/sensor assembly, preferably in the center of the piling core.

FIG. 27 shows the positioning of the sensors 16 in the piling 10, as well as the positioning of the antenna/radio assembly 60 and the antenna assembly 62. A single cable 170 extends between the tip sensors 16 and the housing 61 for the transmission of data within the pile 10. The sensors 16 are positioned preferably using the U-bar suspension assembly 120, 120' or any other suitable system to hold them in position between the strands 12. By locating an antenna on opposing sides, it is always possible to receive an RF signal from the pile, regardless of its orientation.

FIG. 28 shows an alternate preferred arrangement of the sensor and signal transmission system of the piling 10. A tip sensor package 16b, which preferably includes an accelerometer assembly 122 and a strain gauge 124, is located near the tip. At least one antenna 18 is located near the piling top, and an additional sensor package 16a is preferably also located at or near the piling top. Preferred locations for the top and tip sensor packages 16a, 16b based on the piling size are also indicated. Preferably, the tip sensor package 16b includes a non-volatile memory (NVRAM) for storing pile life history data, gauge calibration data and other pile drive related data. This can be included in the electronics module 159 or separately positioned.

The sensor packages 16a, 16b preferably include one of the U-bar suspension assemblies 120, 120' with provisions for holding the accelerometer assembly 122 and a strain gauge 124, which must be positioned within the pile core, as well as the conditioning electronics 159. The U-bar suspension assemblies 120, 120' provide for quicker and easier mounting of the sensors 16a, 16b, reducing assembly time and costs.

In the preferred embodiment shown in FIG. 28, a tube 230, preferably made of plastic material, extends between the tip sensor package 16b and the electronics module housing 61 of the antenna/radio assembly 60. The cable or wire 231 that extends between the tip sensor package 16b and the electronics module housing 61 is run through the tube 230, as shown in FIG. 29.

Figure 30:
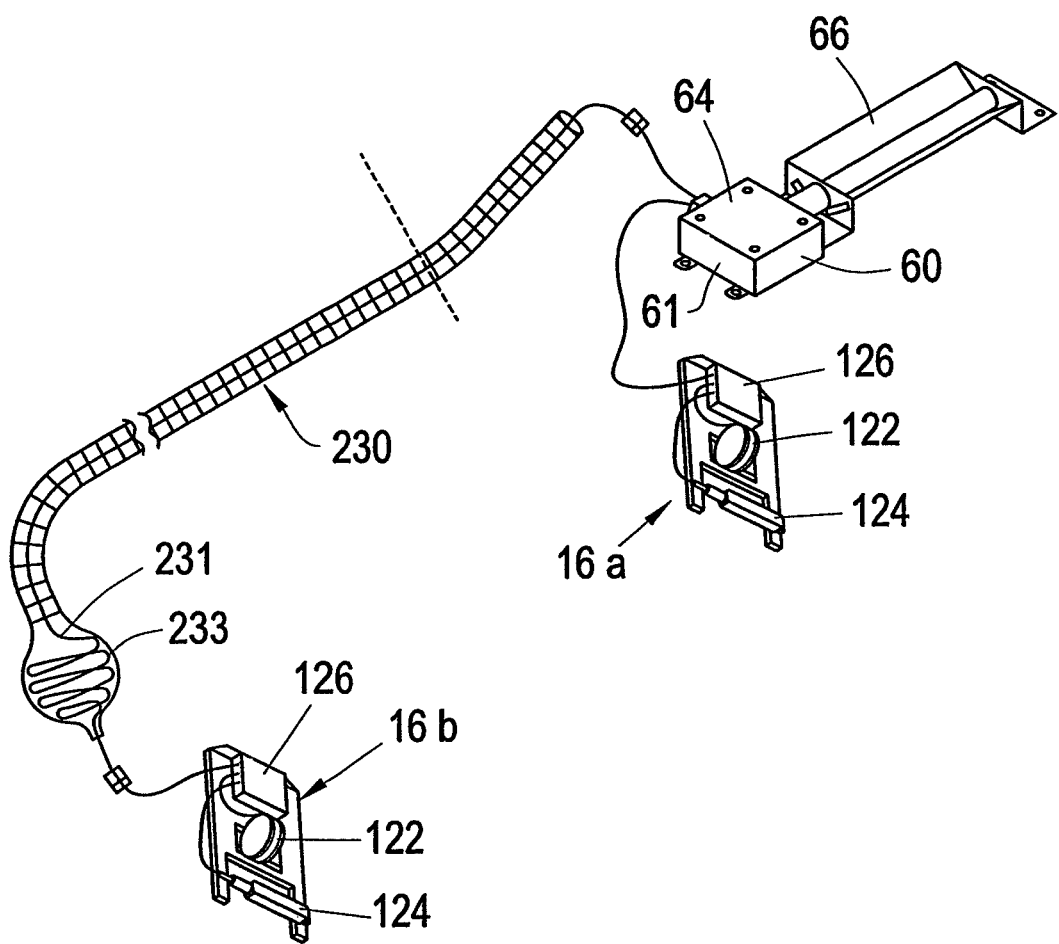
FIG. 30 is a schematic view of the pile sensor and antenna arrangement of FIG. 28 shown without the pile.

FIG. 30 shows a schematic view of this arrangement without the pile 10. An enlarged area or reservoir 233 for an excess amount of the wire or cable 231 is located near or at the tip sensor package 16b. The enlarged area or reservoir 233 can also be in the form of a bulb at the end of the tube 230, and is sealed to the wire or cable 231 that extends toward the sensor package 16b. This allows excess wire or cable 231 to be drawn up from the chamber 233 for splicing in the event that the top of the pile 10 is cut off after installation so that the accelerometer and strain gauge 122, 124 including any other sensors and/or NVRAM located at the tip sensor 16b can still be connected to a networked monitoring node for continued monitoring, as explained in further detail below. Additionally, all of the data stored in the memory located with the conditioning electronics 159 for the sensors in the tip sensor package 16b can be accessed.

Preferably, the tube 230 is tied loosely to the strands 12 down the pile 10 using cable ties or other suitable connectors, as shown in FIGS. 28 and 29, such that the tube 230 is generally held in place but not pinched and the cable or wire 231 is slidable within the tube 230.

Figure 31:
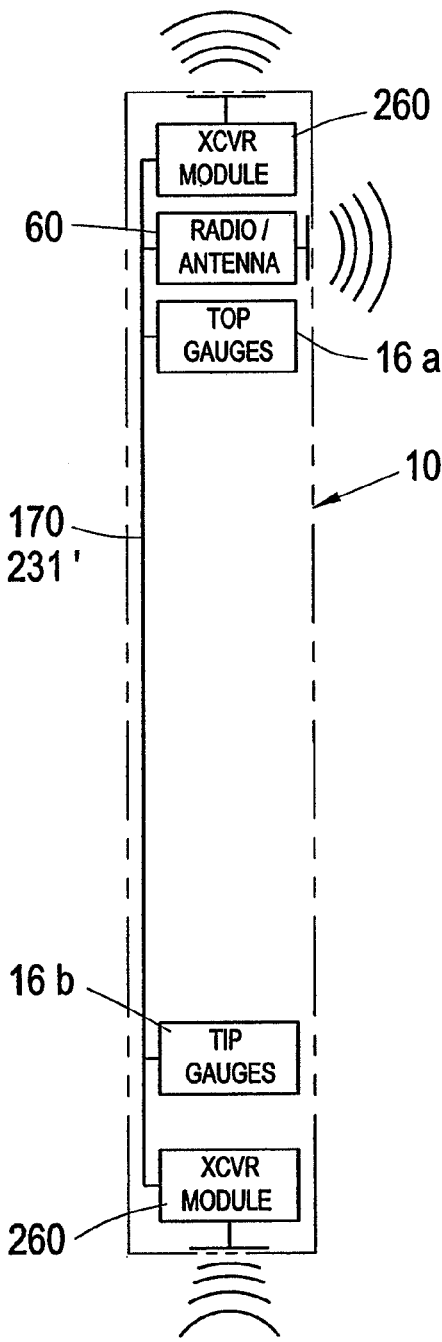
FIG. 31 is a schematic view of a pile showing the common data backbone and an intra-pile transmission system.

Referring to FIG. 31, a schematic view of a pile 10 showing the common data backbone in the form of the cable 170 or 231 is shown. In accordance with a preferred system overview of one embodiment of the invention, a wireless coupling arrangement via fiber optic, RF, magnetic or a hard connection is located at the tips and tops of stacked (or spliced) vertical concrete piles, indicated as transceiver modules 260. This can be provided as an embedded receiver module at the tip of each pile and an embedded transmitter module at the top, and a common connection via a hard-wired link or backbone to move data from the tip to the top of a pile in a pass-through mode. Alternatively, the transceivers 260 can provide bi-directional data, depending on the particular application.

Using this arrangement, data can be relayed and transmitted for monitoring from a below grade pile or spliced through a pile driven on top of it. This allows the collection of information (data) from the various embedded sensing modules in the pile also commonly connected to the hard-wired backbone. Preferably, a method to discern where the transmitted data originated is provided, for example, in the manner of networked nodes.

Additionally, according to the invention, power can be coupled between structures using a special provision of the same interface. This would provide an automatic override of the internal power source should it fail to provide sufficient operating currents. Due to the (sometimes very remote) operating locations, the power source to all structures could also include solar energy obtained from the use of solar panels.

Optionally, it is possible to provide an auxiliary back-up connection port that allows connection of an auxiliary power source, such as a battery in the event of an internal power source failure. External plugs or connections for direct read-out of the data from the accelerometers, strain gauges, temperature sensors, and any other sensors can also be provided through the hard-wired backbone embedded in the concrete structure in the event of a failure of an internal data logger, signal conditioner or transmitter so that the data from the sensors and gauges in the concrete structure could still be collected in the event of a partial system failure.

Central sensor data multiplexing and control including radio interface electronics are preferably provided in the housing 61 or in another housing located within the piling, preferably having an access cover located at the piling surface.

A piling I.D., which preferably corresponds to the radio address or MAC (media access control) address for the transmitter, is stored in the memory along with the date of manufacture, the date of calibration and sensor details, sensor configurations, gain, offset, gauge factor, sensitivity, lot number, serial number, vendor, etc, along with data verifying system QC. This initial information is preferably stored in the non-volatile memory located with the tip gauge conditioning electronics and is further augmented during the piling manufacture at a casting yard by adding information about the pile casting process, such as casting yard, inspector name/number, date of casting, location of piling at casting, concrete modules, concrete specific weight, piling length, diameter or other geometry, temperature profiles (as explained in detail below) and/or strain pre-load, which is recorded in the memory for a later use. Any casting data or other history regarding the forming of the piling can also be recorded so that it will be available later to assist in the driving process. The memory is preferably accessible by the pile foreman to test and/or check the radio prior to and following casting in order to allow QC and any necessary repair prior to shipping and/or driving the piling. The casting yard inspector may also enter critical inspection parameter to be accessed and used during driving of the pile.

All of the data from the memory can be accessed by radio frequency transmission from the piling using one of the antenna assemblies 60, 62 or other types of the antenna assemblies noted above that are located on the pile.

Once at an installation location, it is also possible to log information in the memory with respect to a GPS location of the piling at the time of driving, if available. This can be linked to a known soil property map in order to use the drive data to verify and/or determine soil properties (with the driven pile functioning in the role of a soil probe) and/or to modify the driving process.

The strain and force data gathered by the strain gauge(s) 124 and accelerometer 122 during driving of the piling can be RF transmitted by one of the antenna assemblies 60, 62 for monitoring dynamically during pile driving throughout the driving process. Critical absolute internal strain information can thus be provided during the drive versus the prior known method of external monitoring of relative strain during driving. Specifically, the invention allows monitoring of the actual absolute strain and using that information to ensure that driving forces do not exceed a level that would produce an undesirable tension condition in the piling. This absolute compression and tension stress information is preferably used to provide real time feedback to the hammer or crane operator in order to selectively control hammer energy and optimize the driving process. This information can also be used to prevent overdriving and subsequent pile failure by reporting and providing feedback of the absolute allowable strain readings and ranges.

The inspector, date of drive, date of re-strike, if any, as well as the maximum stress can also be recorded in the memory. This data is then available and trackable with each piling, and can be uniquely time stamped and tracked in the memory in a similar manner to an active read/writable RF I.D. tag which can receive and store data as well as transmit data. Additionally, the drive inspector, civil engineering inspector as well as the pile driving crane operator may be able to access the data in the sensor unit electronics memory during the drive in order to check or verify information with respect to the piling and its history. All of this piling history data is linked as a header to the actual drive data and can be transmitted along with the drive data into a piling database for further lifecycle and/or long term monitoring, QA/QC traceability and accountability purposes. Additionally, this data can be used in connection with future analysis and comparisons to predict faults or failures.

Thus, the entire life cycle of the pile is captured in the non-volatile memory and can be accessed via RF transmission utilizing at least one of the antenna assemblies 60, 62. Additionally, in the case of antenna failure, the housing cover 64 can be accessed from the surface of the piling 10, if necessary, in order to provide a manual electronic connection and/or to replace the battery or electronics module used to drive the sensor unit electronics.

The memory is preferably in the form of a non-volatile RAM, EEPROM, or other writable optic or magnetic media, and is preferably accessed and controlled by a controller. It is also possible that the memory is an expanded memory module used in connection with a known RF I.D. module. Preferably, the sensor unit electronics include a non-volatile memory which can capture data about the sensors as well as other information about the piling being formed. This is utilized in connection with the life cycle tracking of the piling and its related data.

According to the invention, it is also possible to check the concrete strength and readiness through a temperature or curing profile within the concrete structure. Several standards detail this process (ASTM C 1074). Temperature cure profiles can also be saved in the sensor unit electronics memory by providing temperature sensors at the core of the pile as well as at the outer surface. Assuming that the thermal curing temperature flux lines only vary radially outwardly from the core of the pile and remain fairly constant at the same point along the length of the pile, this data can be accurately tracked using the core and surface temperature sensors in order to determine a differential temperature gradient in the pile to determine when the concrete reaches useable strength.

Software may also be used to collect information from the sensory electronics and data loggers for presentation to users based on various established roles such as casting foreman, yard inspector, drive inspector, crane operator, etc. The system is preferably configurable by one role in support of another. For example, the civil engineering inspector may configure the system to flag warnings to the pile driving inspector when specific operational ranges (strain, force, capacity, etc.) are exceeded. This may be applied to the crane operator or other users in order to ensure that specific driving criteria are met or that errors are flagged. The system can also track, count and transmit blows based on a criteria threshold.

Additionally, by positioning gauges at both the top and tip of the pile 10 at a known distance, wave speed anomalies can be detected and used for comparison against certain predefined problematic conditions, such as excessive strain, wave reflections caused by material discontinuities such as a cracked pile, etc. using associated data signatures. When such anomalies are detected or a potential match of anomaly data occurs, the operator can be notified.

In a preferred embodiment, the accelerometer is either AC coupled or DC bias servo controlled to nullify the zero shift effect commonly found in piezoelectric accelerometers. In the application of the preset invention for a piezoelectric (PE) accelerometer, the following application unique conditions are known:

The pile always starts out at velocity equal to zero.

The event being measured has a total cycle time of less than 200 msec.

The pile always returns to velocity equal to zero.

Because prior to and after the event being measured the velocity is equal to zero, and the event being measured occurs in a predetermined and known time interval, AC coupling or the use of a fixed DC bias control using a servo control feedback for the conditioned accelerometer signal prior to data capture works around the zero-shift effect (or error) common to PE accelerometers. This provides for better quality accelerometer data.

Utilizing the present invention, the entire history of a piling along with drive data can be monitored and captured. While the present invention specifically references accelerometer and strain gauge data being captured during the drive, these are only preferred data types, and other types of sensors could also be used to capture and provide other types of data, such as a tip temperature sensor capturing temperatures during the drive, or tip and top temperature sensors being utilized to track a temperature gradient of the pile. Other types of sensors could also be used.

While preferably long-life batteries are utilized in connection with the sensor unit electronics and memory, it is also possible to provide other power sources, such as vibration induced charge, solar power or other means. Additionally, access can be provided for attaching an external power source or replacing the internal power source.

According to the invention, it is also possible to allow the central sensor data multiplexing and control including radio interface electronics to be recovered by removing the housing cover 64. However, the sensor gauges would remain embedded and non-recoverable in the system. This would further reduce costs of the system by providing a means of recovery a portion of the system for re-use.

Figure 32:
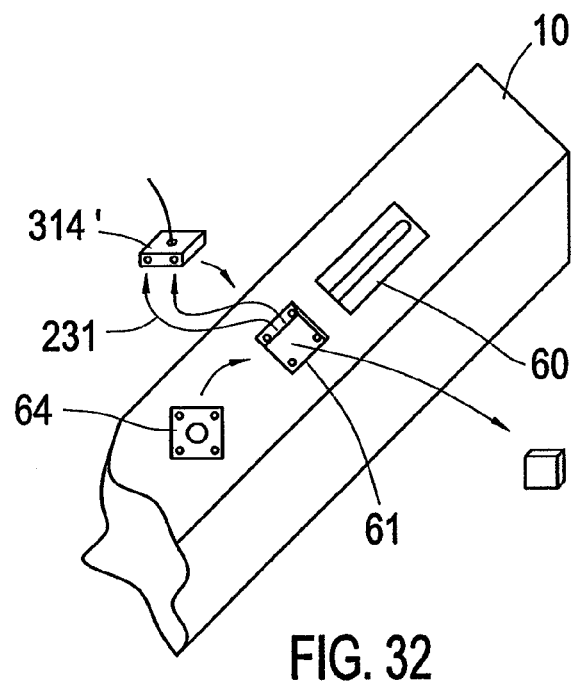
FIG. 32 is a perspective view of a driven piling top having the radio electronics being replaced with a network node module.

Referring now to FIG. 32, in the case where the top of the pile 10 is not cut-off, according to the invention the pile 10 is reconfigured for long-term monitoring by removing the radio module from the electronics module housing 61 of the antenna/radio assembly 60. A replacement and externally powered networked monitoring node 314' is then installed in the housing 61 and connected to any available tip/top gauge cables or wires 231.

Figure 33:
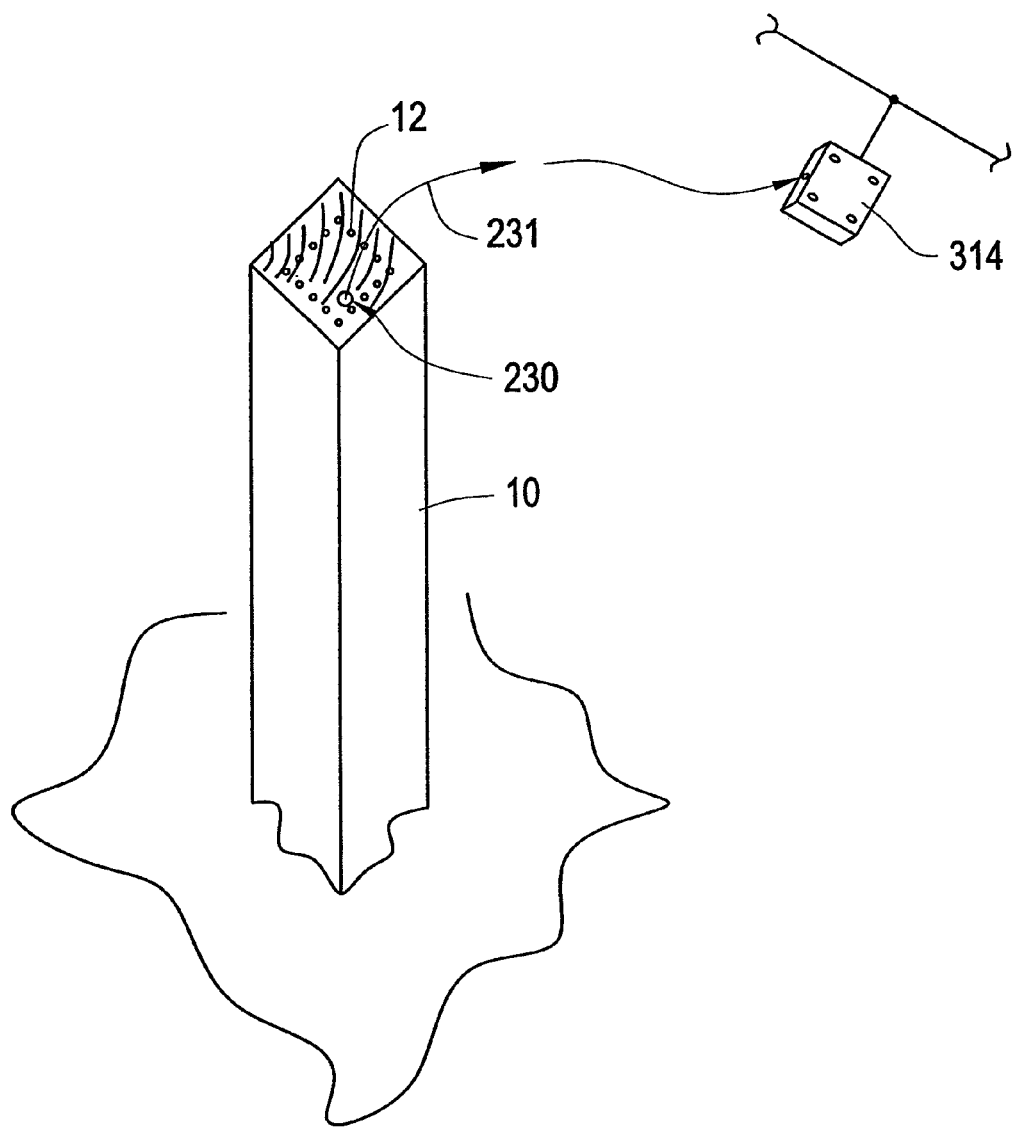
FIG. 33 is a perspective view of a piling with the top cut off, showing the connection with a network node module.
Figure 34A:
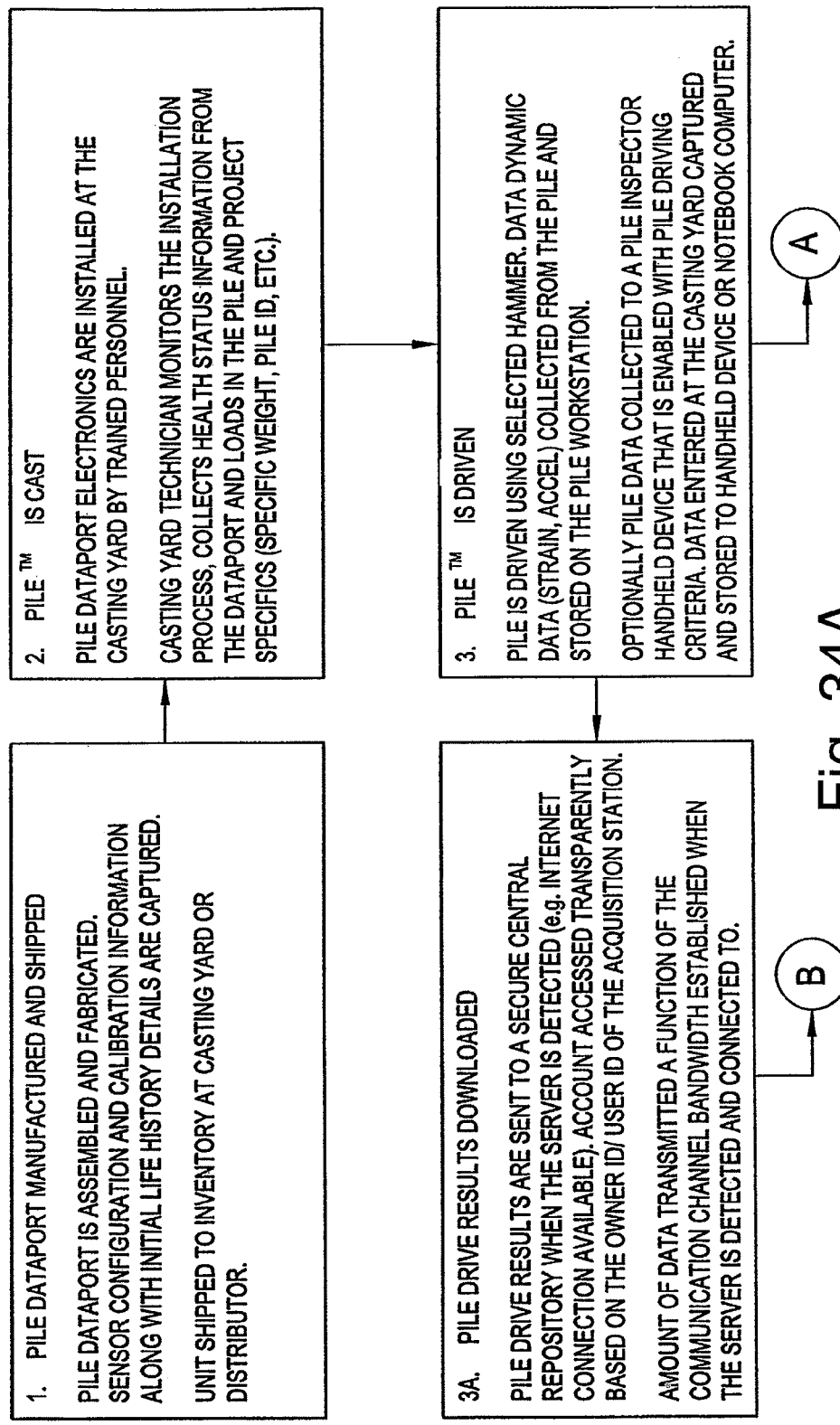
FIGS. 34A-34C are a flow chart showing the life cycle monitoring system in accordance with the present invention.
Figure 34B:
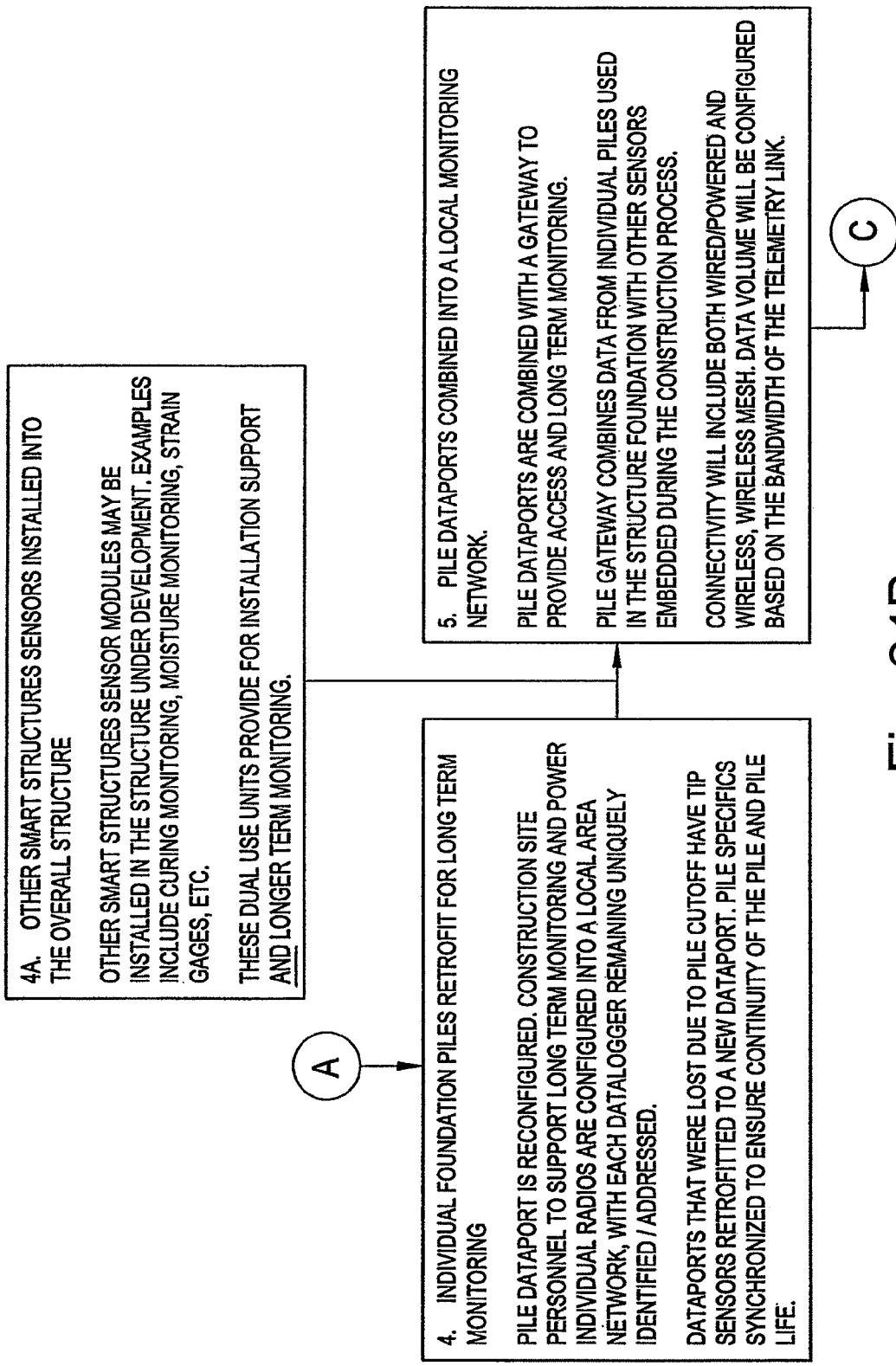
Figure 34C:
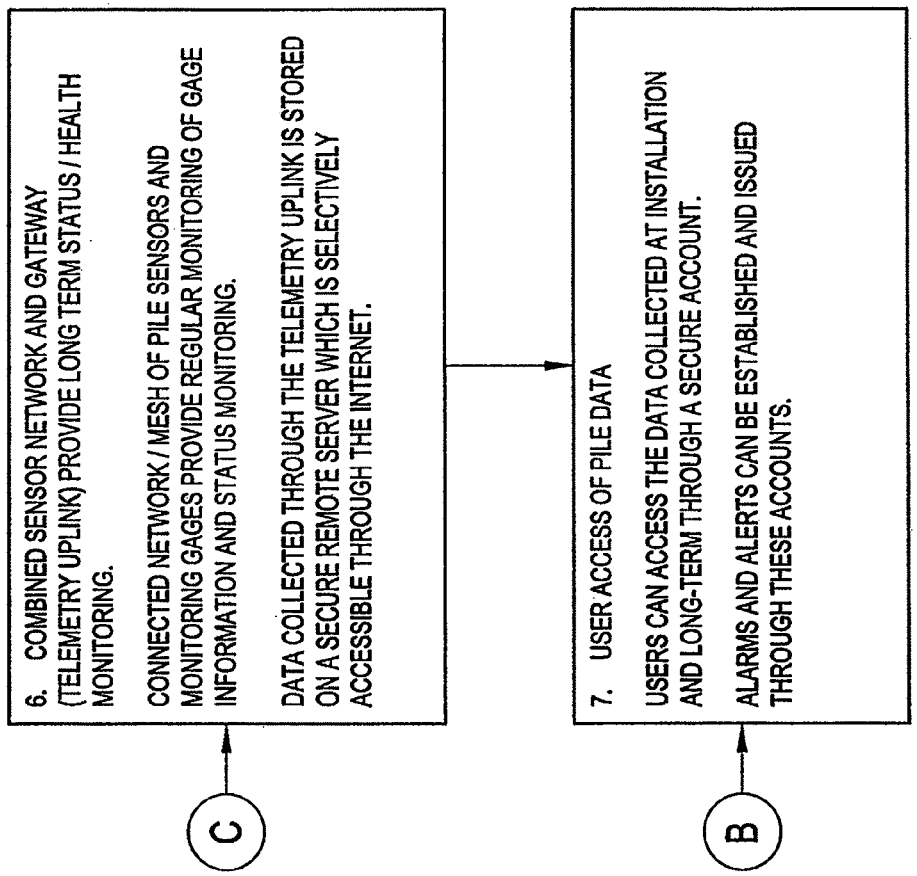

Referring now to FIG. 33, the pile 10 is shown after being driven, with the top of the pile removed to a cut-off elevation based on the application requirements. In order to provide further monitoring throughout the life cycle of the pile 10 and its subsequent make-up of a structure or foundation and to be able to access information in the memory located with the tip sensor package 16b, the wire or cable 231 can be pulled up from the reservoir 233 after the pile top is cut off and can then be spliced to a connector or cable that is connected to a networked monitoring node 314, which can be embedded in a capping structure or otherwise located in proximity to the pile 10. This can be done by a site technician. Accordingly, if the pile 10 is driven and the top is cut off, and regardless of where this occurs below the top gauges 16a, there will always be a cross section of the tube 230 containing the cable 231 exposed, as shown in FIG. 33.

Figure 35:
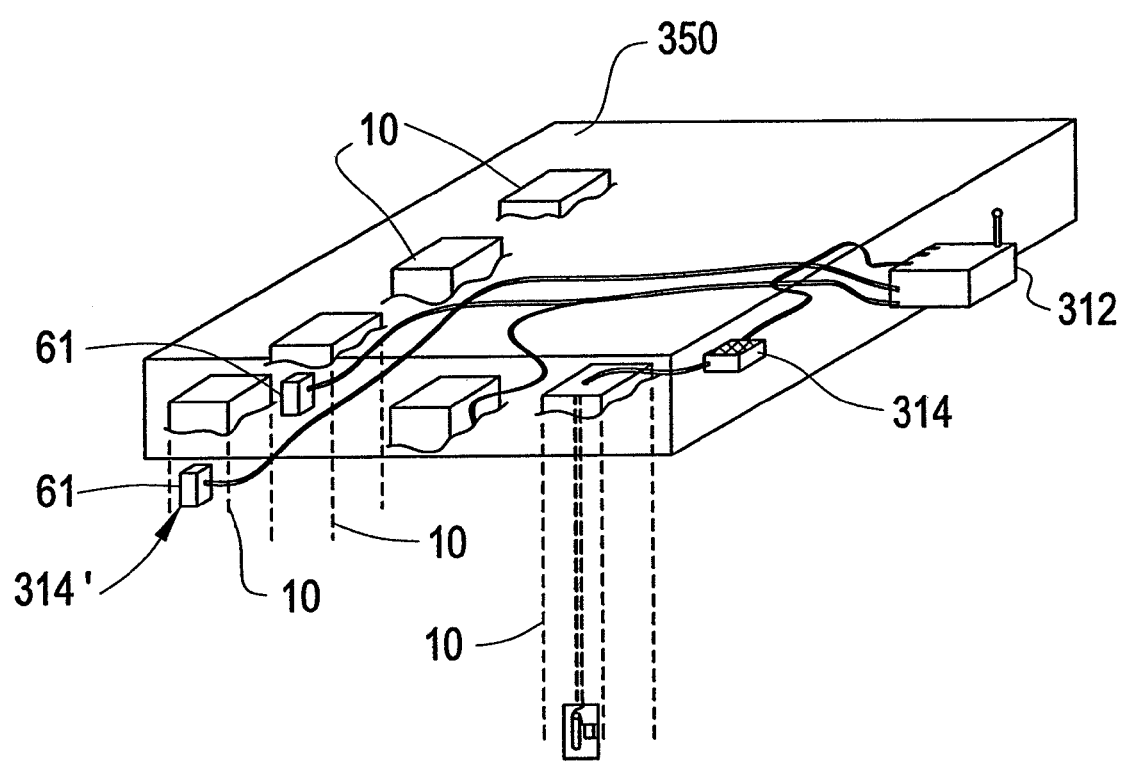
FIG. 35 is a perspective view of the a concrete cap cast over a plurality of piling tops that have monitoring sensors that are connected together to a node for connection to additional members of the structure and/or telemetry uplink for data acquisition and monitoring.

Referring now to FIGS. 34A to 34C and 35, life cycle monitoring of the pilings according to the present invention is provided. This is done by retrofitting the individual piling antenna/radio assembly 60 with a networked monitoring node capability. This provides a method for establishing a powered local area network of select sensor-enabled pilings 10 and other sensors. These retrofitted nodes or dataports can be located in the electronics module housing 61 prior to casting the concrete cap 350, as shown in FIG. 35, and include a mechanism for self-configuring all of the connected piling nodes in the piles and concrete structures that make up the transportation/building foundation and superstructure. The nodes or dataports are preferably interfaced using a typical network protocol. Additionally, power is distributed by the system to all of the gauges/sensors being monitored. Alternatively, the power distribution and networking functionality can be combined.

According to the invention, construction personnel will either replace or augment the existing piling data ports located in the electronics module housing 61 with a wired network that provides power and a wired connection for data transfer. The nodes that are added to this network preferably self configure and report up either in a peer-to-peer or master-host configuration. The network and/or wiring provides redundancy and addressability that ensures at least a subset of the connected piles are available and/or accessible.

These newly networked pilings 10 making up a foundation can be connected to a larger network or telemetry uplink such as GPRS, wired broadband, PowerLine networking, etc. 312, as shown in FIG. 35.

Historical life information concerning each pile 10 (including the dynamic installation details/results) will be logically transferred from the piles 10 and the tip sensor package 16b now providing long term monitoring.

All uploaded telemetry information from the drive and for the long term monitoring of the pile 10 will be kept at a remote central repository for review, monitoring, and reporting.

The system also provides a means of retaining the unique addressing information of a given radio, preferably by logically linking it to the sensor address ID, or through other means of synching or mapping the radio ID being replaced with the backbone ID of the replacing networked monitoring node 314.

The current piling sensor(s) 122, 124 to networked monitoring node 314 connectivity is accomplished using low power differential signaling for pilings 10. While more tolerant to radio and materials interference, a digital signaling architecture would better eliminate any chances of interference and decouple the Radio/Monitoring modules from the transducer transfer function. According to the invention, a digital bus architecture will be utilized for all sensors used in the system. In this configuration:

Sensor details and calibration information are kept at the tip sensor's conditioning electronics, with the digital bus providing a means of communicating sensor calibration and sensor data and all NVRAM contents;

A shared bus is used allowing multiple gauges and various uniquely identified gauge types to share the same physical wired backbone;

A high speed and power efficient bus protocol is used to address the volume of data from each of the gauges:

A smart plug-and-play system is used to allow multiple gauge configurations to be used, automatically identifying and self configuring based on the gauges present;

In the event that the Radio/Monitoring module 60 must be removed, the configuration/calibration of the gauges and life history of the pile 10 is retained or mirrored by electronics (such as a NVRAM) provided with the tip sensor 16b electronics for continued use by the replacement networked monitoring module 314.

The invention provides long term monitoring capability through the tip gauge data as well as data stored in the conditioning electronics NVRAM, regardless of the final pile configuration. In addition to the networked monitoring nodes 314 encapsulated in the cap 350, strain gauges and other sensors can also be located in the cap 350 and connected with additional network nodes for cap gauges and sensors. This can be connected with the gateway 312 so that cap data can be captured and transmitted along with pile data. Further monitoring capabilities, for example for monitoring additional structures, such as a pier or a roadbed located on the cap 350 shown in FIG. 35 can also be provided. These additional monitoring capabilities can be carried out by providing nodes with self adapting network capabilities. Thus, monitoring of all of the elements in a given structure can be carried out through the use of a stackable network topology built upon the basic pile monitoring system described in detail herein. This provides a system or structure where the pile sensors are wired along with other sensors into a cap, which is then wired along with other sensors into a pier, which is then wired along with other sensors into a roadbed, ultimately providing data for a partially or completely integrated structure (including one or more of the noted components and/or other structural components) via a telemetry uplink.

Figure 36:
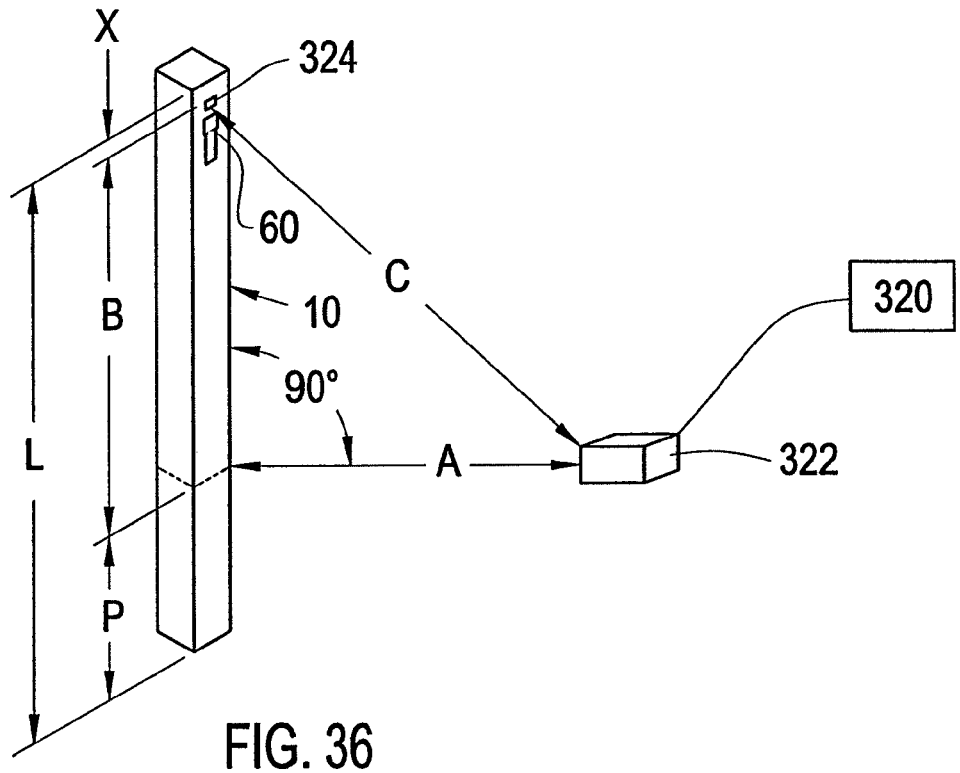
FIG. 36 is a perspective view of a system for tracking a penetration depth of a piling according to the invention.

Referring now to FIG. 36, an improved means for determining pile penetration and ultimately the load bearing capacity of the piling according to the invention is provided. The current means of determining pile penetration (and ultimately capacity) of a concrete pile involve manually putting markings on one side of the pile and an inspector who is responsible for counting the pile hammer blows (via a saximeter) and noting the movement/penetration of these marks moving past an elevation reference marker. This process requires effort and personnel involvement throughout the course of the drive. The present invention can automatically and accurately count the hammer blows through gauge 122, 124 excitation beyond a set threshold within the pile 10 internally or from signals received and interpreted by a tracking/monitoring device, such as a Pile Workstation (SPW) 320, which is a centralized system controller that collects real time drive data from the sensors and gauges within the piles 10, interfaces with the height sensing pile penetration system, described below, tracks blow counts (internally or externally) and calculates and synchronizes blows per displacement with the dynamic data collected during the pile drive to communicate information to the inspector in real time for controlling the drive as well as providing real time pile load capacity data.

Tracking the displacement of the pile 10 according to the invention can be carried out by one of several methods.

In a first method, a laser lidar "time of flight" and triangulation concept is utilized coupled to a SPW 320. In this configuration, a laser lidar system 322 is first projected level to a reference elevation relative to a vertical standing pile 10 to determine the adjacent side of a right triangle A. The lidar system 322 is then pivoted up the face of a vertical standing pile to a reference point 324 near the top of the pile 10 to determine the corresponding hypotenuse C of the right triangle. The vertical height of the pile 10 above the reference elevation is based on the distance B from the reference elevation up to the reference point 324 located at a known distance X down from the top. Knowing the overall length L of the pile 10, as well as the dynamically calculated distance B and the distance X, the pile penetration P below the reference elevation can easily be calculated. The change in height can easily be determined based on the change in C.

The reference marker 324 at the top of the pile 10 would be constructed to facilitate automatic vertical tracking in the case of a vertically standing pile and self alignment adjustment by the pivoting lidar head (via a motorized servo control system). A retro-reflective line or mirrored object can be utilized.

The lidar system 322 would continually compensate by locking on the reference marker 324 for the downward movement of the reference marker target as the pile is being driven. The system dynamically provides raw real time calculated pile height B or calculated pile penetration P data to a tracking monitoring device SPW 320. This used in conjunction with the blow count being derived by the internal gauge system would be used to calculate/record/track the blows/foot, providing for fully automated tracking.

Alternatively, the lidar is projected to a common point at the top of the pile 10, which includes the possibility of putting the reference marker on the hammer or cap, after having obtained a distance orthogonal to the standing pile (length) surface at the reference elevation. The pile penetration is continuously determined by subtracting the measured pile height above the reference elevation (determined from triangulation) from overall pile length L. A vertically repositioning scanning system (in the case of vertically extending piles)

is preferably used to account for a continually shortening height. It is also possible for the system be able to sweep the pile from top to bottom to determine the angle of the standing pile and project to a point non-orthagonal to the pile at the reference elevation and to then use known trigonometric techniques to determine the necessary data This can be coupled with SPW 320 to replace the inspector's need to physically collect pile drive data. The SPW 320 counts or keeps track of blows and synchronizes this data relative to pile penetration data to then calculate the blows per displacement based on the calculated pile penetration P.

Alternatively, an IR based sensor time of flight camera could be used to detect and reference the centroid of a predetermined point on the hammer or the pile, such as the pile cushion, using thermal imaging. Additionally, a pivoting camera system using 3D image sensing and pattern recognition could also be used as a target identifier to replace the lidar head referenced above.

Figure 37:
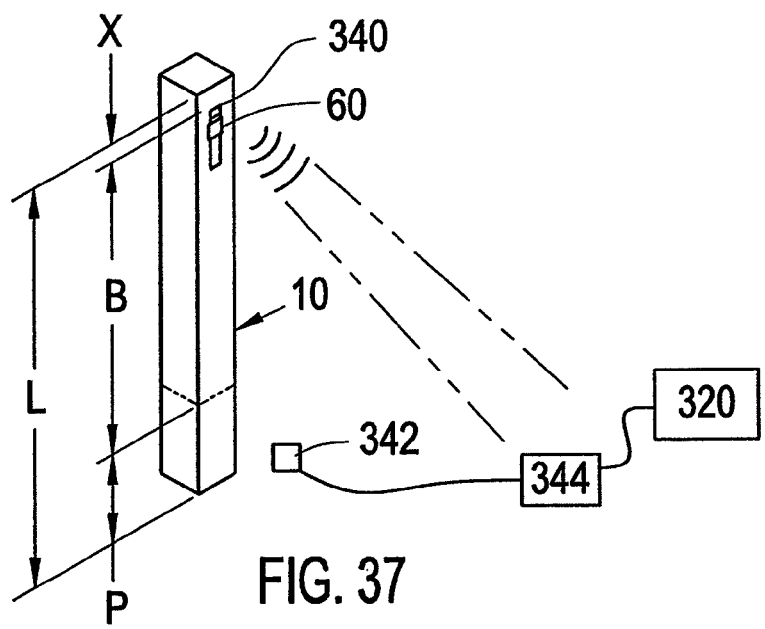
FIG. 37 is a perspective view of an alternate system for tracking a penetration depth of a piling.

A second method of determining the penetration depth of the driven pile is through the use of barometric altimeters, as shown in FIG. 37. Two barometric altimeters 340, 342 provide two measurements each: barometric pressure and altitude. In general, when measuring altitude, barometric altimeters can be used over short periods after calibration, and are constantly recalibrated to zero-out the barometric pressure changes caused by changing weather patterns. Some systems do this by getting altitude information from GPS satellites, knowing the difference is barometric pressure. According to the invention, a digital barometric altimeter 340 is mounted on the piling 10 or on the hammer or cap (with stand alone communication), and is preferably removably mounted at the electronic module housing 61 and interfaces with one of the radio's digital channels. The height B is then determined by differentially comparing the transmitted data from the pile or hammer mounted altimeter 340 with another barometric altimeter 342 mounted down at the fixed reference elevation (or other known elevation), such as the previous pile depth marker string. Measuring the outputs of the altimeters 340, 342 differentially effectively removes the common-mode or absolute barometric pressure from the equation, and provides a pure differential localized altitude or relative barometric pressure reading during the course of the drive. Raw data is preferably collected by a monitoring device 344 that receives the signals from both altimeters 340, 342 in a fashion similar to that described above. The height is supplied by the altimeters or calculated in the SPW 320. Preferably, the altimeters 340, 342 are calibrated relative to each other at the same elevation prior to use to zero out tolerance errors. The communication from the altimeters 340, 342 can be to the monitoring device 344 using wireless or wired connections and/or can be directly with SPW 320 using the radio/antenna assembly 60 for the pile mounted altimeter 340 and a separate wired or wireless connection from the reference elevation altimeter 342, depending on the location. The bottom altimeter 342 can be located away from the pile 10 at the job site as long as it is maintained at the reference elevation.

While these approaches assume piles are driven co-linear with gravity, corrections and adjustments can be made through the use of an inclinometer and triangulation for the case of angled piles. It is common for piles carrying high lateral loads to be driven at an angle of up to 45° (batter piles). In this instance, an inclinometer is used to determine compensation angles and the penetration depth is calculated using known trigonometric techniques.

While the preferred embodiments of the invention have been described in detail, the invention is not limited to the specific embodiments described above, which should be considered as merely exemplary. Further modifications and extensions of the present invention may be developed, and all such modifications are deemed to be within the scope of the present invention as defined by the appended claims.

The invention claimed is:

1. A method of monitoring pilings, comprising:
inserting a sensor package between strands or reinforcements in a piling form to position sensors in a core area of a piling;
connecting a radio module to the piling, the radio module being in communication with the sensor package;
casting the piling;
determining the strain pre-load and recording it for later use;
driving the piling and obtaining data from the sensor package during driving;
at least one of monitoring the data obtained from the sensor package during driving and monitoring and using the data during the driving to adjust driving parameters for the pile; and
using absolute internal strain information from the data obtained from the sensor package located inside the piling core to maximize driving efficiency in real time during driving of the piling.

2. The method of claim 1, further comprising:
monitoring absolute internal strain information to ensure that driving forces do not exceed a level that would produce a damaging tension stress condition in the piling.

3. The method of claim 1, further comprising:
monitoring absolute internal strain information for changes in pre-load during driving; and
using this information to predict piling failure.

4. The method of claim 1, further comprising:
inserting the sensor package at a tip of the piling and inserting a second sensor package at a top of the piling.

5. The method of claim 1, further comprising:
detecting wave speed anomalies using the data and a known distance between the sensors in the piling; and
comparing the wave speed anomalies against pre-defined conditions for failure detection.

6. The method of claim 1, further comprising:
storing the data obtained from the sensor package in a memory.

7. The method of claim 1, further comprising:
transmitting the data obtained to a piling history database for further lifecycle and long term monitoring.

8. The method of claim 7, further comprising:
cutting off a top of the piling; and
pulling excess wire or cable located inside a hollow tube from a wire reservoir in proximity to a piling tip in order to connect the sensor package located at a tip of the piling to the networked monitoring node.

9. The method of claim 1, further comprising:
retrofitting the piling installing a networked monitoring node that is connected to the sensor package;
retaining unique addressing information of a given piling, by logically linking a sensor package address ID; and
connecting the node to an external gateway for data transmission for long term monitoring.

10. A method of long-term monitoring for pilings, comprising:
forming a cast concrete piling with a sensor package located in a core area of the piling;
determining a strain pre-load and recording it for later use;
driving the piling and obtaining data from the sensor package during driving;

retrofitting the piling by installing a networked monitoring node that is connected to the sensor package;
retaining unique addressing information of a given piling, by logically linking a sensor package address ID; and
connecting the node to an external gateway for data transmission for long term monitoring.

11. The method of claim 10, further comprising:
storing pile data in a memory located in the piling.

12. The method of claim 11, further comprising:
for a pile having the top cut off after driving, pulling excess wire or cable located inside a hollow tube from a wire reservoir in proximity to a tip wire or cable reservoir in order to connect a tip sensor package to the networked monitoring node.

13. The method of claim 10, further comprising:
providing a GPS at the pile;
obtaining a location for the pile; and
obtaining soil properties for the location.

14. The method of claim 10, further comprising:
providing a re-writable memory in the piling; and
storing and updating data in the re-writable memory.

15. A suspension assembly for positioning at least one sensor between strands in a concrete structure, comprising:
first and second U-shaped frames connected to one another;
at least one strand engaging member located on each of the U-shaped frames facing away from one another and adapted to engage opposing reinforcement strands or bars of a concrete structure;
a slidable carrier attached to the frames for supporting at least one gauge;
the first and second U-shaped frames are spring biased away from one another; and
centering springs extend between the slidable carrier and the frame for movably sliding the slidable carrier to a centered position on the U-shaped frames, the slidable carrier including provisions for attaching sensors.

16. The suspension assembly of claim 15, wherein at least one of the strand engaging members is formed of a spring material.

17. The suspension assembly of claim 15, further comprising:
a strain gauge connected to the slidable carrier.

18. The suspension assembly of claim 15, further comprising:
an accelerometer connected to the slidable carrier.

19. A suspension assembly for positioning at least one sensor between strands in a concrete structure, comprising:
first and second U-shaped frames connected to one another;
at least one strand engaging member located on each of the U-shaped frames facing away from one another and adapted to engage opposing reinforcement strands or bars of a concrete structure,
a slidable carrier attached to the frames for supporting at least one gauge;
a first opening with at least two opposing V-shaped side walls for registration with a first sensor housing located in the slidable carrier or a mounting plate connected thereto; and
a second opening defined in the slidable carrier or the mounting plate connected thereto for a second sensor.

* * * * *